(12) United States Patent
Onofiok et al.

(10) Patent No.: US 9,296,988 B2
(45) Date of Patent: Mar. 29, 2016

(54) THREE-DIMENSIONAL CELL ADHESION MATRIX

(75) Inventors: Ekama Onofiok, Sacramento, CA (US); Kit S. Lam, Davis, CA (US); Juntao Luo, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 817 days.

(21) Appl. No.: 13/378,540

(22) PCT Filed: Jun. 18, 2010

(86) PCT No.: PCT/US2010/039241
§ 371 (c)(1),
(2), (4) Date: Jun. 28, 2012

(87) PCT Pub. No.: WO2010/148346
PCT Pub. Date: Dec. 23, 2010

(65) Prior Publication Data
US 2012/0322145 A1 Dec. 20, 2012

Related U.S. Application Data

(60) Provisional application No. 61/218,805, filed on Jun. 19, 2009.

(51) Int. Cl.
*C12N 5/00* (2006.01)
*C09J 129/04* (2006.01)
*C08K 5/55* (2006.01)

(52) U.S. Cl.
CPC ............. *C12N 5/0062* (2013.01); *C09J 129/04* (2013.01); *C08K 5/55* (2013.01); *C12N 2533/30* (2013.01)

(58) Field of Classification Search
CPC . C12N 5/0062; C12N 2533/30; C09J 129/04; C08K 5/55
See application file for complete search history.

(56) References Cited

U.S. PATENT DOCUMENTS

2003/0185787 A1 10/2003 Hubbell et al.

FOREIGN PATENT DOCUMENTS

WO    WO 2007/124132    11/2007

OTHER PUBLICATIONS

Ivanov, A.E., et al.; Polymer, 2004, vol. 45, p. 2495-2505.*
Zhang, D., et al.; Langmuir, 2007, p. 8806-8809.*
Hersel, U., et al.; Biomaterials, 2003, p. 4385-4415.*
International Search Report and Written Opinion dated Feb. 23, 2011, issued in related International Patent Appln. No. PCT/US2010/039241, filed Jun. 18, 2010.
Konno et al., "Temporal and spatially controllable cell encapsulation using a water-soluble phospholipid polymer with phenylboronic acid moiety," 2007, Biomaterials, vol. 28, No. 10, 1770-1777.
Choi et al., "Surface immobilization of biocompatible phospholipid polymer multilayered hydrogel on titanium alloy. Colloids and Surfaces," 2008, Biointerfaces, vol. 67, No. 2, pp. 216-223.

* cited by examiner

*Primary Examiner* — Robert Jones, Jr.
(74) *Attorney, Agent, or Firm* — Kilpatrick Townsend and Stockton LLP

(57) ABSTRACT

The present invention provides a cell adhesion matrix having poly(vinyl alcohol) chains crosslinked via carboxy phenyl boronic acid crosslinkers. The cell adhesion matrix can also include a molecular recognition element bound to the poly (vinyl alcohol) chains via a carboxy phenyl boronic acid group, as well as including cells. The present invention also provides a method for making and de-gelling the cell adhesion matrix.

15 Claims, 18 Drawing Sheets

4: Bis-amino-carboxyphenyl boronic acid-PEG
(PEG-diboronic acid crosslinker)

6: Bis-(amino-lysine-dicarboxyphenylboronic acid)-PEG
(PEG-tetraboronic acid crosslinker)

5: Polypropyletheramine-tricarboxyphenyl boronic acid
(PPO-triboronic acid crosslinker)

9

EDTA

DTPA

THREE-DIMENSIONAL CELL ADHESION MATRIX

CROSS-REFERENCES TO RELATED APPLICATIONS

This application is the U.S. National Stage entry under §371 of International Application No. PCT/US2010/039241, filed Jun. 18, 2010, which claims priority to U.S. Provisional Application No. 61/218,805, filed Jun. 19, 2009, which are incorporated in their entirety herein for all purposes.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Three-dimensional (3D) tissue culture systems which emulate key physical and molecular features of the extracellular microenvironment, provide tremendous advantages to tissue engineering. An important goal in engineering such materials is the ability to present cell-instructive mechanical and biochemical cues which influence cell fate. Integrins (heterodimeric, transmembrane receptors for extracellular matrix (ECM) proteins) "integrate" mechanochemical information from the ECM with the intracellular environment, activating intracellular signaling cascades which govern many cellular functions, including proliferation, motility, and survival, and thus, are excellent biological targets for manipulating cell fate in 3D culture systems. Typical integrin-targeting gel matrices used for 3D tissue culture incorporate reconstituted matrix proteins such as collagen and hyaluronic acid, all of which have disadvantages associated with protein purification, processing, cost, and poor control over physical properties of the gel. The use of Matrigel (a commercially available, laminin-rich extracellular matrix (ECM)) in 3D tissue modeling, for example in vitro modeling of mammary tumors, also presents numerous challenges, as cell fate in these systems is influenced by a number of undefined, poorly characterized, and highly variable bioactive components. Fully synthetic, bioactive 3D systems incorporating adhesive peptides such as the integrin-binding arginine-glycine-aspartic acid (RGD) sequence found in many ECM proteins, have also been reported, however, these systems lack the complexity of molecular information critical for supporting many cell functions in vitro. Accordingly, development of synthetic biomaterial scaffolds with defined bioactive molecular recognition elements and fine-tunable mechanical properties, offers tremendous advantages to the field of 3D tissue modeling and bioengineering.

Surprisingly, the present invention meets this and other needs. The present invention shows that bioactive hydrogels can be used to culture a number of cognate integrin-expressing tissue types including both normal and malignant human mammary epithelial cells, colon adenocarcinoma, and endothelial cells; and possesses suitable biochemical complexity for eliciting similar morphogenic patterns as those observed in Matrigel, but with the additional advantages of being purely synthetic and void of any animal products, well-characterized and consistent, such that the various molecular elements which influence cell fate can be easily and reproducibly identified.

BRIEF SUMMARY OF THE INVENTION

In one embodiment, the present invention provides a cell adhesion matrix prepared by the process of contacting a plurality of poly(vinyl alcohol) chains and at least one boronic acid crosslinker having at least two boronic acids in a mixture, under conditions such that each boronic acid becomes linked to two adjacent hydroxy groups of one of the plurality of poly(vinyl alcohol) chains.

In another embodiment, the present invention provides a cell adhesion matrix including at least one boronic acid crosslinker having at least two boronic acids linked by a Linker having a biocompatible polymer, and a plurality of poly(vinyl alcohol) chains, wherein each boronic acid is linked to two adjacent hydroxy groups of one of the plurality of poly(vinyl alcohol) chains.

In other embodiments, the present invention provides a method for preparing a cell adhesion matrix, the method including contacting a plurality of poly(vinyl alcohol) chains and at least one boronic acid crosslinker having at least two boronic acids in a mixture, under conditions such that each boronic acid becomes linked to two adjacent hydroxy groups of one of the plurality of poly(vinyl alcohol) chains, thereby preparing the cell adhesion matrix.

In another embodiment, the present invention provides a cell adhesion matrix prepared by the process including contacting a molecular recognition element conjugate of formula (III), wherein the molecular recognition element is LXY3, MSE, HYD1, LLP-2A, or RGD ligand, and a plurality of poly(vinyl alcohol) chains of formula (II), wherein subscript n is from about 10 to about 5000, at a pH of about 7.4, such that each boronic acid of the molecular recognition element conjugate becomes linked to two adjacent hydroxy groups of one of the poly(vinyl alcohol) chains to form a plurality of modified poly(vinyl alcohol) chains. The process also includes contacting the plurality of modified poly(vinyl alcohol) chains and a carboxy phenyl boronic acid crosslinker of formulas Ia, Ib, Ic or Id, at a pH of about 7.4 such that each boronic acid becomes linked to two adjacent hydroxy groups of one of the plurality of modified poly(vinyl alcohol) chains.

In a further embodiment, the present invention provides a method of de-gelling the cell adhesion matrix of the present invention, by contacting the cell adhesion matrix with a de-gelling agent.

BRIEF DESCRIPTION OF THE DRAWINGS

FIG. 7a shows human umbilical vein endothelial cells in the overlay cultures at day 16 grow in "sheets" in PVA-dbPEG hydrogels in the absence of tethered integrin ligands (left image); the cells form branching clusters in the presence of RGD and LXY3 peptides tethered to the hydrogel scaffold (right image). FIG. 7b shows branching tubulogenic morphology of HUVEC cells overlaid on lrECM observed at 24 h (left), with regression of tube-like structures by day 5 (right). Images for FIGS. 7a and b were captured using 20× and 10× objective lens, respectively. Scale bar for 7b measures 50 µm.

DETAILED DESCRIPTION OF THE INVENTION

Figure 1:
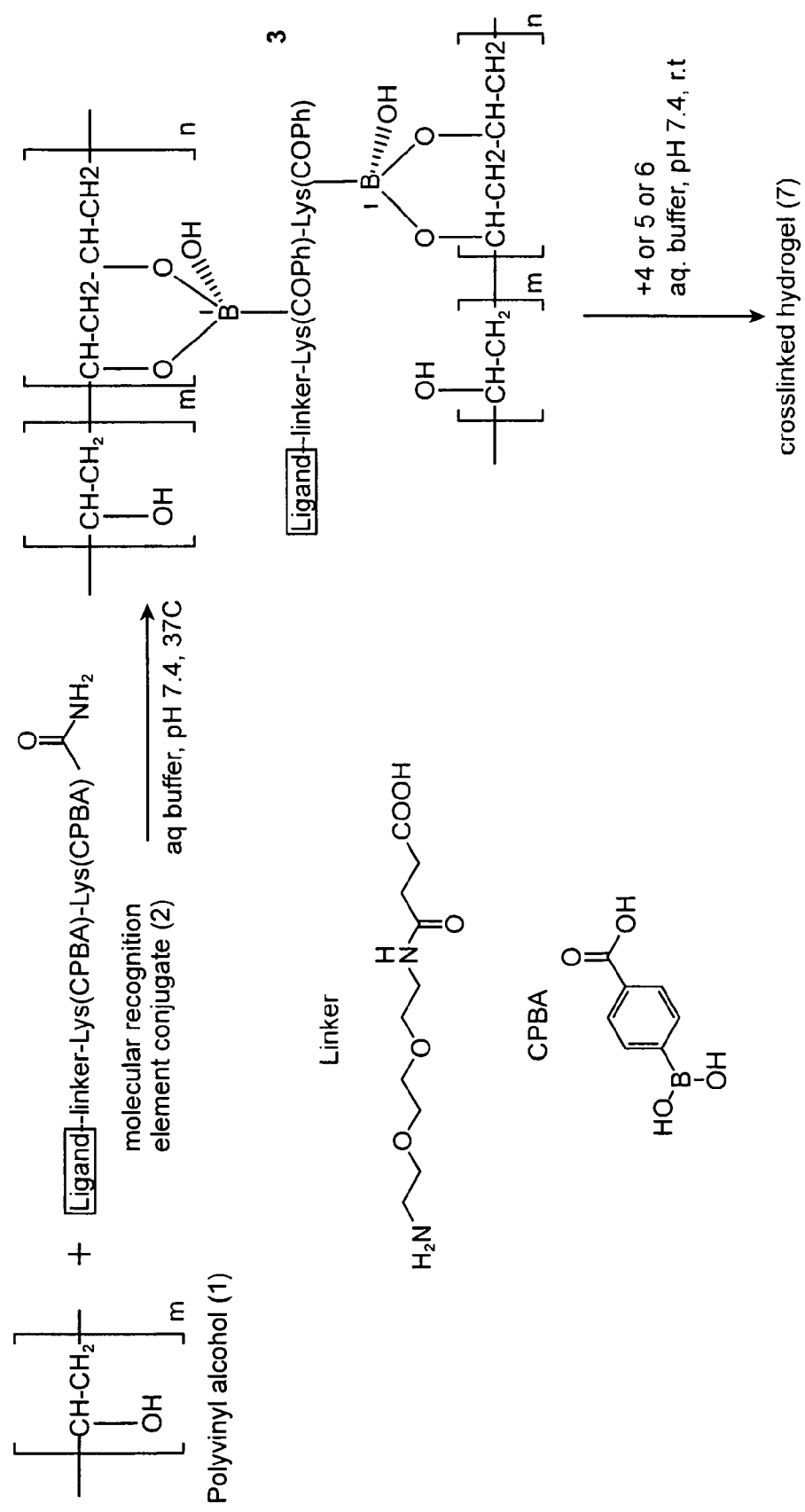
FIG. 1 shows a scheme for the preparation of the cell adhesion matrix of the present invention.
Figure 2:
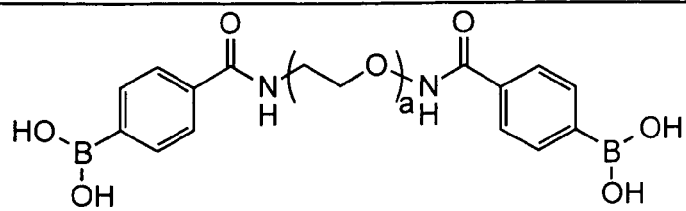
FIG. 2 shows examples of the carboxy phenyl boronic acid crosslinker of the present invention.
Figure 2:
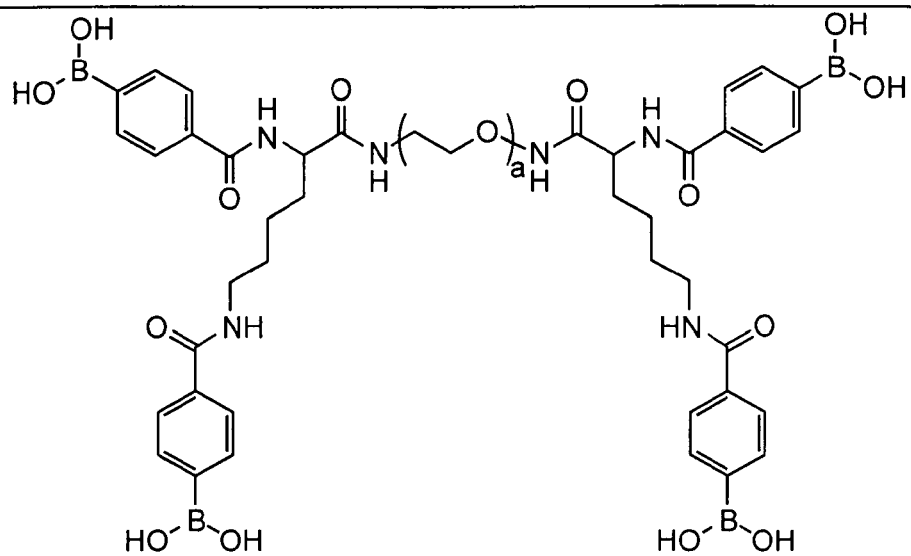
Figure 2:
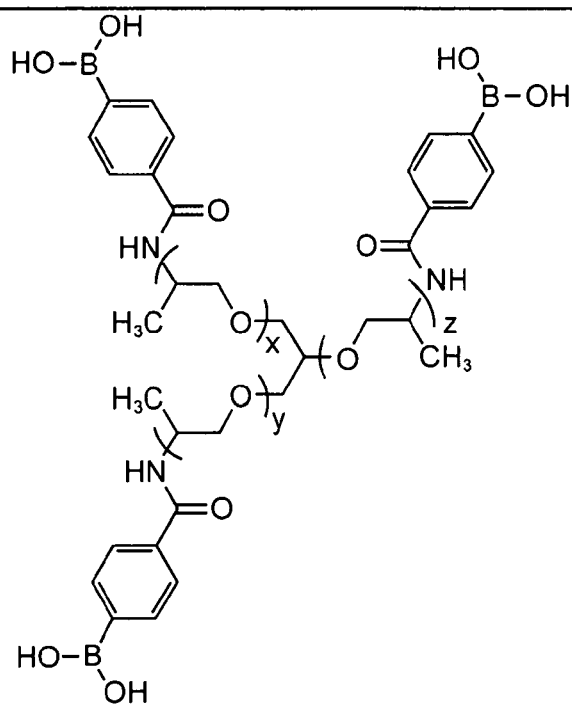
Figure 3:
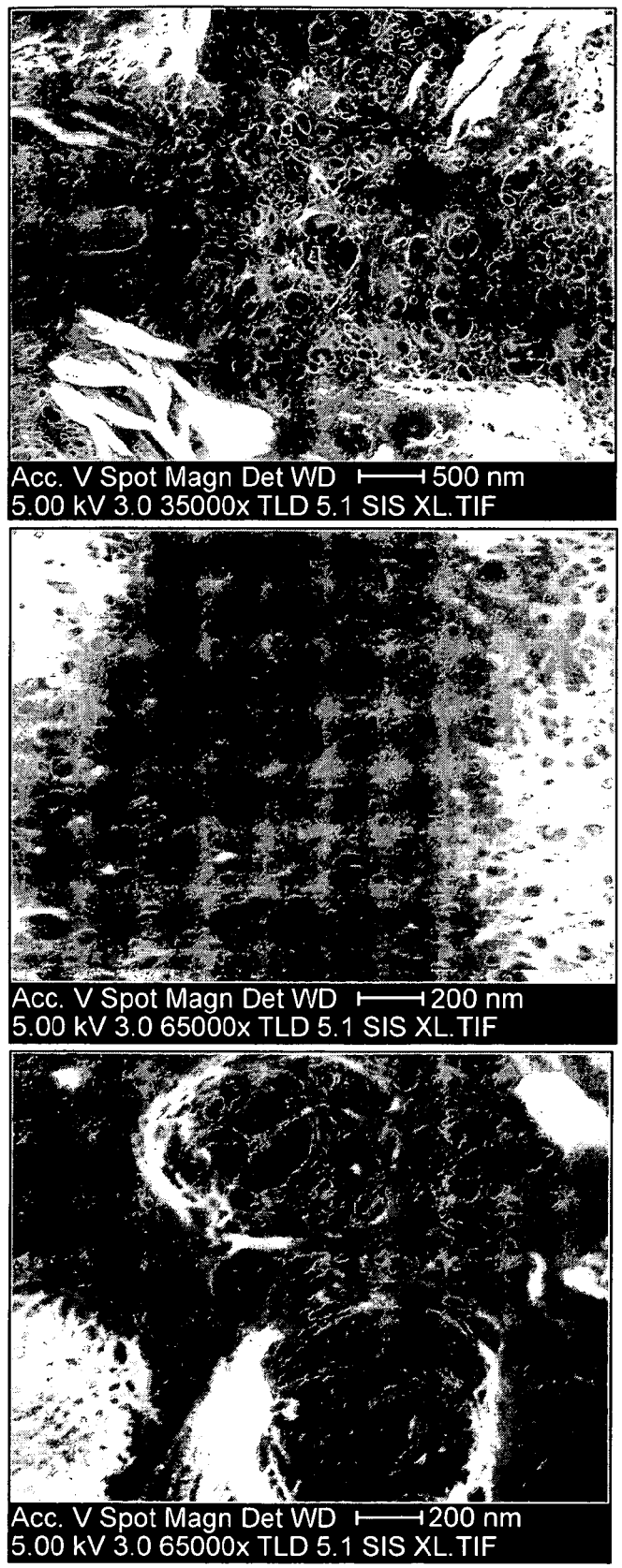
FIG. 3 shows scanning electron micrographs (surface topology) of freeze-dried hydrogel showing nanofibrous, porous meshwork. Scale bars measure 200 nm (and 500 nm for the leftmost image).
Figure 4:
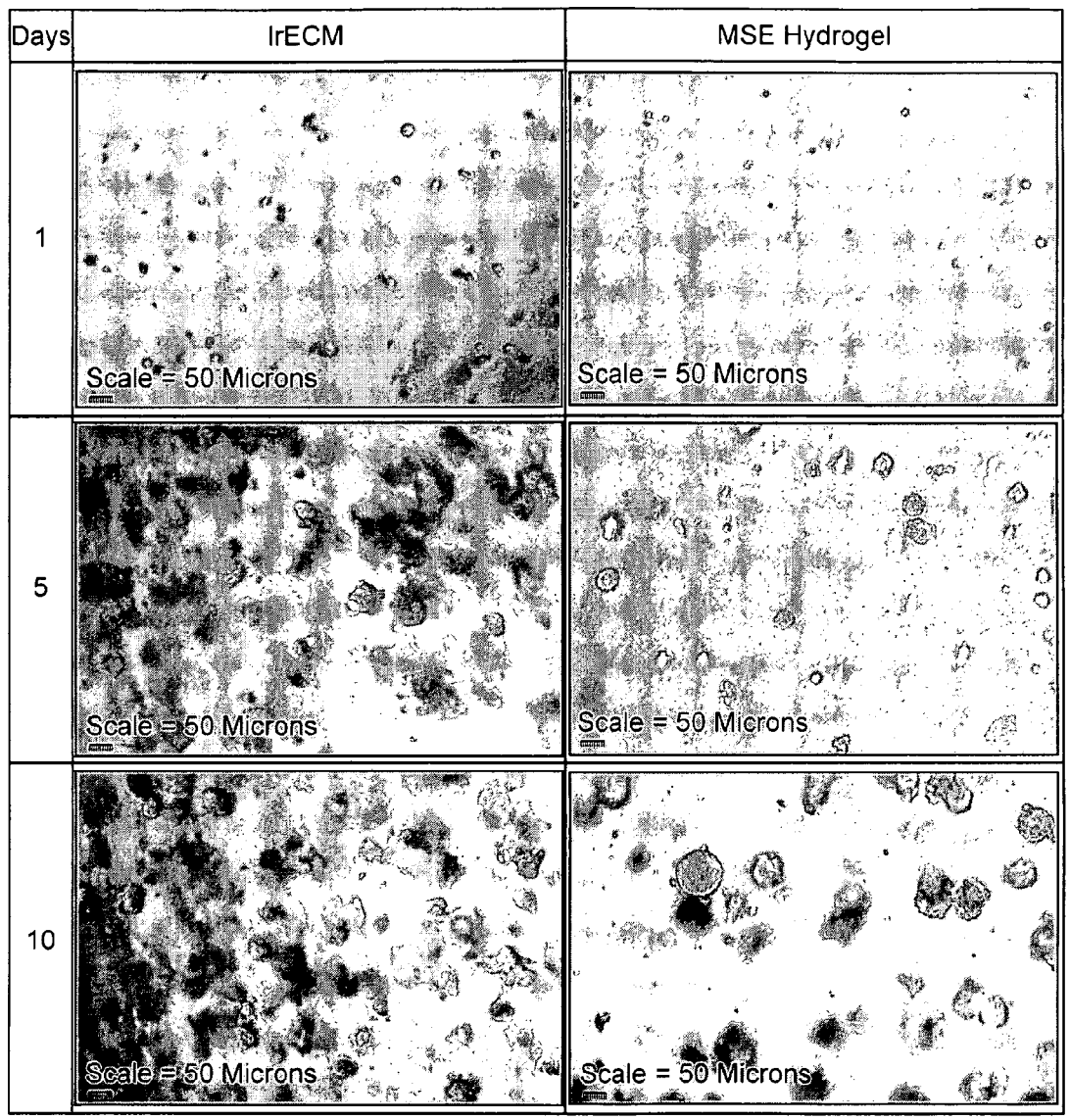
FIG. 4 shows phase-contrast micrographs of HT-29 cells in MSE-functionalized hydrogels, and laminin-rich extracellular matrix (lrECM) captured at days 1, 5 and 10 of encapsulation. Scale bars measure 50 µm.
Figure 5:
FIG. 5 shows HT-29 cell colonies extracted from the hydrogel after 11 days in 3D culture. On the left is a phase contrast image of colonies in 3D before fixation and extraction. Center and right images show extracted colonies immunostained for $\alpha_6$ integrin (dark), and via nuclear DAPI staining (light), confirm multicellularity of spheroids extracted from the hydrogel.
Figure 6:
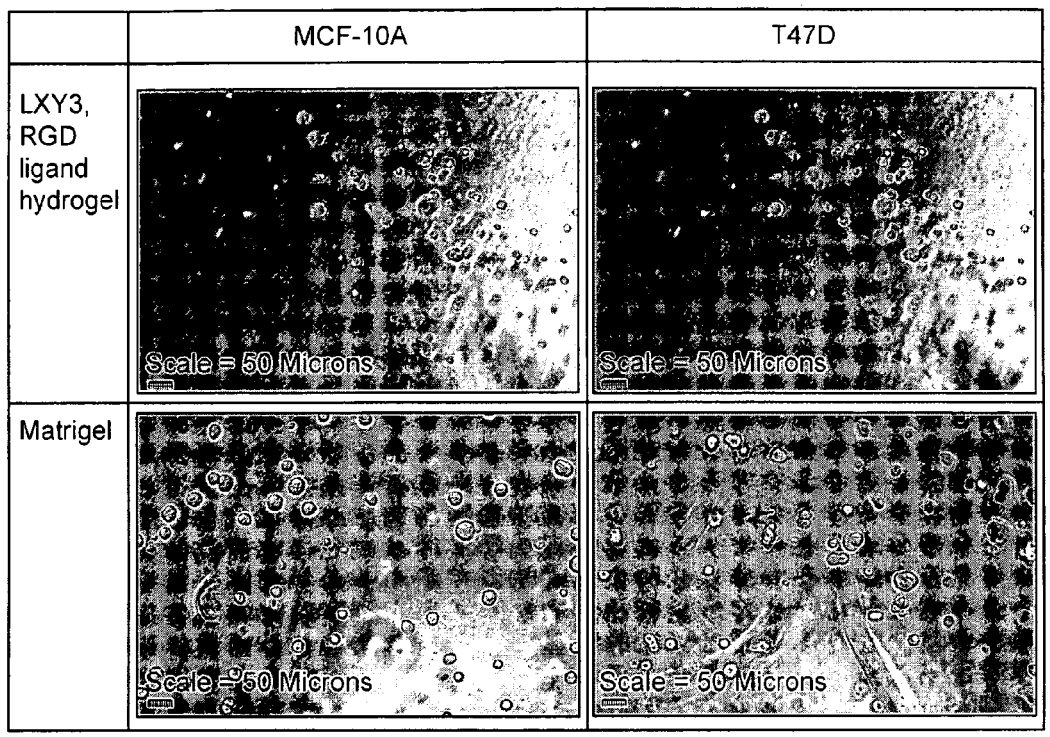
FIG. 6 shows morphogenesis of normal and malignant mammary epithelial cells in 3D culture using the overlay method: on top row are mammary epithelial cultures in PVA-dbPEG hydrogels functionalized with $\alpha_3\beta_1$ and $\alpha_v\beta_3$ integrin-targeting ligands (LXY3 and LXW7 peptides, respectively). Phase contrast micrographs show spheroid morphogenesis of MCF-10A (normal mammary) cells (left image) and T47D (mammary ductal adenocarcinoma) cells (right image). Bottom row depicts the same cell lines cultured in lrECM (Matrigel). Scale bar measures 50 µm.
Figure 7:
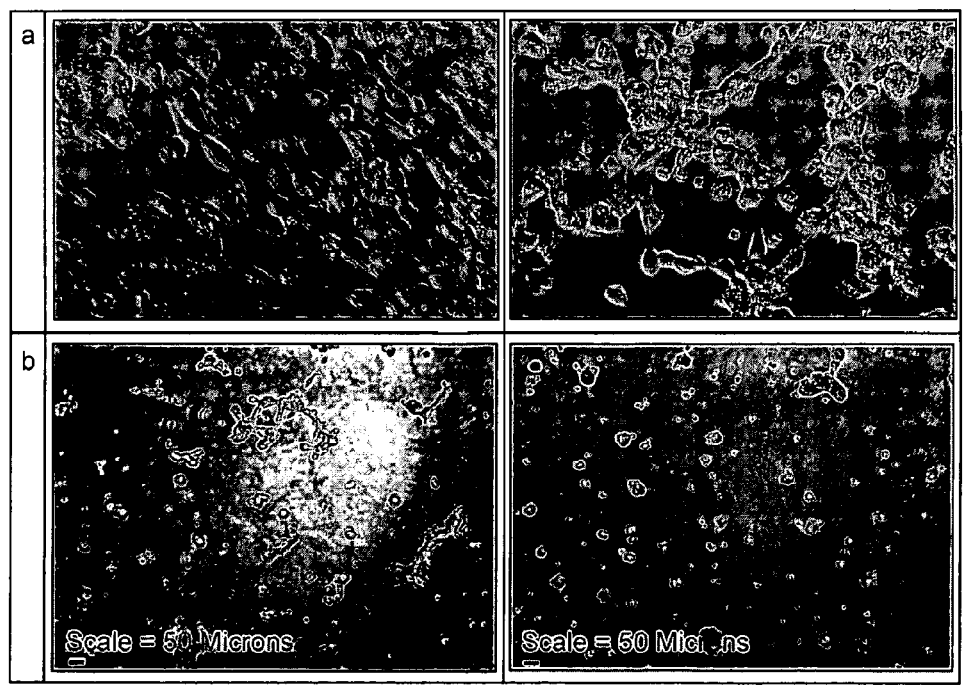
FIGS. 7a and 7b show tube morphogenesis of HUVEC cell line in 3D culture.

The present invention provides a series of purely synthetic, "made-to-order" hydrogels, rendered bioactive by their incorporation of molecular recognition elements such as cell surface integrin receptor ligands, as novel biomaterial scaffolds for 3D culture and tissue engineering. The degradable, nanofibrous hydrogels are comprised of high molecular weight polyvinyl alcohol (PVA) scaffolds functionalized with high-affinity cell adhesion ligands against naturally expressed or cell-transfected $\alpha_6\beta_1$, $\alpha_3\beta_1$, $\alpha_4\beta_1$, $\alpha_5\beta_1$, $\alpha_v\beta_3$, $\alpha_1$, $\alpha_2$, and other integrins, and cross-linked via cyclic complexation of boronic acid crosslinkers with polyhydroxyls on PVA. Mechanical properties of the hydrogel can be fine-tuned via alteration of crosslink density using a number of biocompatible di, tri- or tetra-boronic acid-modified polymers. Hydrogel formation occurs rapidly at room temperature and physiological pH, and thus facilitates simultaneous encapsulation of cells in situ within the forming hydrogel. Alternatively, cells can be seeded and maintained in culture atop a pre-formed gel. Extracellular matrices suitable for 3D culture of different cell types can be made to order by combinatorially incorporating a number of molecular recognition elements, such as ligands which target to cell-expressed integrins, into the hydrogel matrix. Finally, crosslinking of the bioactive PVA scaffold is reversible in the presence of a cis-diol competitor, such as fructose, facilitating non-enzymatic degradation of the hydrogel matrix and rapid extraction of cells from 3D culture for other biological applications.

I. DEFINITIONS

As used herein, the term "cell adhesion matrix" refers to a 3-dimensional matrix culture system that emulates physical and molecular features of the extracellular microenvironment. The cell adhesion matrix of the present invention is formed by crosslinking poly(vinyl alcohol) chains using boronic acid crosslinkers having at least two boronic acid groups where the boronic acids bind to two adjacent hydroxy groups of the poly(vinyl alcohol) chains. The boronic acid can be any boronic acid species, such as carboxy phenyl boronic acid.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "poly(vinyl alcohol) chains" refers to polymer chains of poly(vinyl alcohol). The poly(vinyl alcohol) chains can have any molecular weight, and are described in more detail below.

As used herein, the term "crosslinked" refers to the state of having numerous poly(vinyl alcohol) chains interconnected to each other via the boronic acid crosslinkers such that they become a single structure. The chemical functionality that links the individual poly(vinyl alcohol) chains that are crosslinked, is termed a "crosslinker". A crosslinker is typically a multifunctional compound that reacts with at least one functional group on one poly(vinyl alcohol) chain and one reactive functional group on another poly(vinyl alcohol) chain, thereby linking the two poly(vinyl alcohol) chains to each other. The crosslinkers of the present invention can have more than two crosslinking groups.

As used herein, the term "boronic acid crosslinker" refers to a chemical moiety having at least two boronic acid groups that can crosslink the poly(vinyl alcohol) chains by binding to two adjacent hydroxy groups on the poly(vinyl alcohol) chains. The boronic acid crosslinker can also include a linker having a biocompatible polymer (see within).

As used herein, the term "Linker" refers to a chemical moiety that links the carboxy phenyl boronic acid groups together. Linkers useful in the present invention have a biocompatible polymer. The term "biocompatible polymer" refers to a polymer that is non-toxic in animals. Examples of biocompatible polymers include, but are not limited to, poly (ethylene glycol), poly(propylene glycol) and others. Polyether polymers useful in the present invention include poly (ethylene glycol) (PEG) and poly(propylene glycol) (PPG). The PEG and PPG can be modified with a branching moiety. The term "branching moiety" refers to a chemical moiety that links to the polyether polymer via one functional group, and provides at least two other functional groups for linking to the boronic acid groups. Examples of branching moieties include, but are not limited to, lysine, serine, threonine, tyrosine, and cysteine. Other branching moieties can be a lysine derivative, having a carboxylic acid group and both an alpha and omega amine. Other branching moieties are known to one of skill in the art.

As used herein, the term "molecular recognition element conjugate" refers to a conjugate of a molecular recognition element and at least one boronic acid. The molecular recognition element can be any species capable of recognizing a biological species, such as a cell, peptide, protein, oligonucleotide or antibody. For example, the molecular recognition element can be a cell adhesion ligand such as a peptide, protein, peptidomimetic or antibody, or a reporter substrate such as a fluorescent substrate. Examples of cell adhesion ligands useful in the present invention include RGD ligands, LXY3, MSE, HYD1, and LLP-2A. These ligands, and others useful in the present invention, bind to various integrin types, including $\alpha_6\beta_1$, $\alpha_3\beta_1$, $\alpha_4\beta_1$, $\alpha_5\beta_1$, $\alpha_v\beta_3$, $\alpha_1$, $\alpha_2$, among others. The boronic acid groups (see within) of the molecular recognition element conjugate can bind to the poly(vinyl alcohol) chains of the cell adhesion matrix of the present invention. The boronic acid can be linked to the molecular recognition element by a variety of means known to one of skill in the art.

As used herein, the term "de-gelling" refers to the breaking of the crosslinking bonds that hold the matrix together. The de-gelling is accomplished using a de-gelling agent that replaces the poly(vinyl alcohol) hydroxy groups of the boronate esters. The de-gelling agent can be any cis-diol compound. Cis-diol compounds are those having a 1,2-cis-diol, such as fructose. Other cis-diol compounds are useful in the present invention.

A "binding group" is a functional group capable of forming a covalent linkage with another group. Binding groups can include boronic acid moieties, and those groups suitable for click chemistry, such as alkynes and azides. Other binding groups can be found in Bioconjugate Techniques, Greg T. Hermanson, Academic Press, 2d ed., 2008 (incorporated in its entirety herein).

II. CELL ADHESION MATRIX

The present invention provides a cell adhesion matrix for tissue engineering. The cell adhesion matrix is a poly(vinyl alcohol) matrix that is crosslinked using a biocompatible polymer having at least two boronic acid groups. At a pH of about 7.4, the boronic acid forms a boronate ester with adjacent hydroxy groups of the poly(vinyl alcohol), thereby crosslinking the poly(vinyl alcohol) polymer chains and forming the cell adhesion matrix. A molecular recognition element conjugate can be linked to the poly(vinyl alcohol) chains, either before or after formation of the matrix. For example, the poly(vinyl alcohol) chains can be chemically modified, such as via covalent modification, with a molecular recognition element prior to crosslinking.

In some embodiments, the present invention provides a cell adhesion matrix prepared by the process of contacting a plurality of poly(vinyl alcohol) chains and at least one boronic acid crosslinker having at least two boronic acids in a mixture, under conditions such that each boronic acid becomes linked to two adjacent hydroxy groups of one of the plurality of poly(vinyl alcohol) chains.

In another embodiment, the mixture includes a plurality of cells. The cells can be any type of cell, including, but not limited to human epithelial cells, endothelial cells, embryonic stem cells, induced pluripotent stem cells, hematopoietic stem and differentiated cells, mesenchymal stem cells, stem-cell derived cardiomyocytes, keratinocytes, mammary epithelial cells and malignant cells of many tissue origins, including mammary ductal carcinoma, colon adenocarcinoma, pancreatic adenocarcinoma, and prostate adenocarcinoma cells. In some embodiments, the cells are induced pluripotent stem cells. In other embodiments, the cells are mammary epithelial cells (MECs).

In some other embodiments, the conditions include a pH of from about 7.0 to about 8.0. In still other embodiments, the conditions include a pH of about 7.4.

In other embodiments, the boronic acid is a carboxy phenyl boronic acid. Other boronic acid groups are useful in the present invention.

In some other embodiments, the boronic acid crosslinker is of formula I:

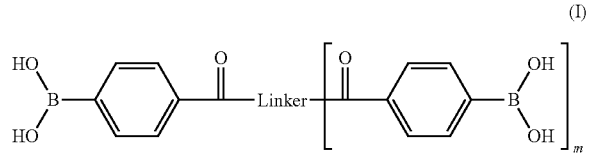

(I)

wherein the radical Linker of formula I includes a biocompatible polymer. Subscript m of formula I is from 1 to about 100. Each poly(vinyl alcohol) chain of the cell adhesion matrix is of formula II:

(II)

wherein subscript n of formula II is from about 10 to about 5000.

The Linkers useful in the present invention can be linear polymers, branched polymers, dendrimers, hyperbranched polymers, star polymers, and others. When the Linker is a linear polymer, the crosslinking groups can be at the ends of the polymer as well as along the length of the polymer. Other Linkers include multi-functional compounds such as EDTA and DTPA, as well as a tri-amino triazine, either alone or in combination with polymers such as PEG and PPG. Other Linkers useful in the present invention are known to one of skill in the art.

Biocompatible polymers useful in the present invention are those that are non-toxic to animals. Examples of biocompatible polymers include polyethers such as poly(ethylene glycol) and poly(propylene glycol), as well as cellulose, polysaccharides, and polyesters. One of skill in the art will appreciate that other biocompatible polymers are useful in the present invention.

The poly(vinyl alcohol) chains used in the cell adhesion matrix of the present invention can be any suitable size. For example, the poly(vinyl alcohol) chains can have a molecular weight of from about 500 to about 150,000, or from about 50,000 to about 150,000, or from about 75,000 to about 125,000, or from about 85,000 to about 105,000. Other poly(vinyl alcohol) chains are useful in the present invention. The poly(vinyl alcohol) can also be modified with a binding group to facilitate functionalization with the molecular recognition element conjugate. For example, when click chemistry is utilized, the poly(vinyl alcohol) can be functionalized with azides to facilitate the click chemistry.

In some embodiments, the Linker of formula I includes a poly(propylene glycol) polymer. In other embodiments, the Linker of formula I includes a poly(ethylene glycol) polymer of the following formula:

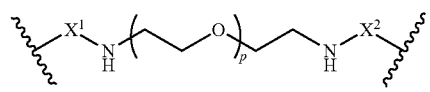

wherein radicals $X^1$ and $X^2$ are each independently a bond, a branching moiety, lysine or a lysine derivative. And subscript p is from about 10 to about 500, preferably from about 10 to about 100, more preferably from about 10 to about 50.

The poly(ethylene glycol) polymer useful in the present invention can be any suitable size. For example, the poly(ethylene glycol) polymer can have a molecular weight of from about 500 to about 50,000, or from about 500 to about 5,000, or from about 1,500 to about 2,500. Other poly(ethylene glycol) polymers are useful in the present invention. In some embodiments, subscript p, or any of subscripts a, b, c, x, y or z, is such that the PEG can have a molecular weight of from about 500 to about 50,000, or from about 500 to about 5,000, or from about 1,500 to about 2,500.

The branching moiety of the present invention provides at least two functional groups for linking to the boronic acid groups. Examples of branching moieties include, but are not limited to, lysine, serine, threonine, tyrosine, ornithine, cysteine, diaminopropionic acid, glutamic acid and aspartic acid. Other branching moieties can be a lysine derivative, having a carboxylic acid group and having both an alpha and omega amine.

In other embodiments, radicals $X^1$ and $X^2$ are each a bond. In some other embodiments, radicals $X^1$ and $X^2$ are each lysine. In some other embodiments, subscript p is from about 23 to about 68. In still other embodiments, subscript p is from about 34 to about 57. In yet other embodiments, subscript p is from about 40 to about 50.

The ratio of poly(vinyl alcohol) and boronic acid crosslinker in the process of the present invention can be any suitable ratio. For example, the ratio of boronic acid crosslinker to PVA can be from about 100:1 to about 1:100 (wt/wt). The ratio can also be from about 10:1 to about 1:10 (wt/wt), or about 9:1, 8:1, 7:1, 6:1, 5:1, 4:1, 3:1, 2:1, 1:1, 1:2, 1:3, 1:4, 1:5, 1:6, 1:7, 1:8, or 1:9. In some embodiments, the ratio is 1:1 (wt/wt).

In other embodiments, the boronic acid crosslinker has the following formula Ia:

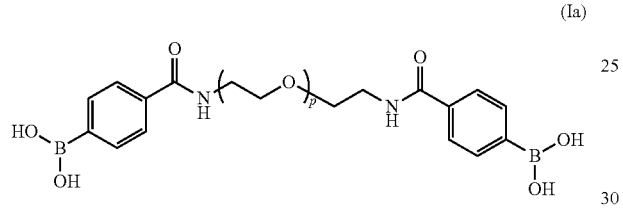

(Ia)

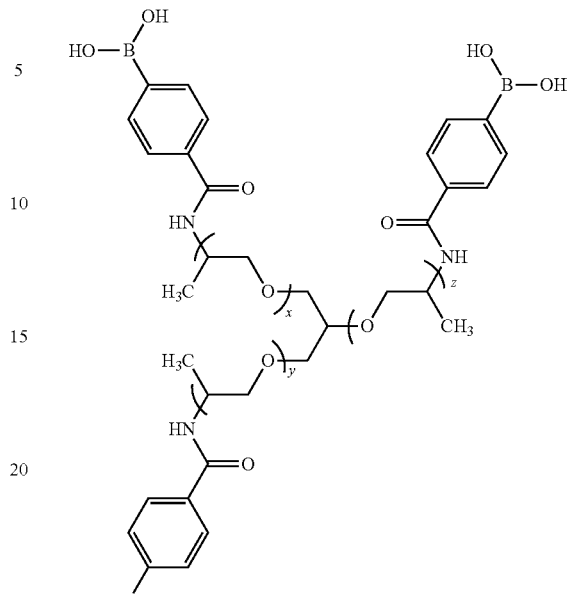

(Ic)

wherein subscript p is from about 10 to about 1000, preferably from about 10 to about 100, more preferably from about 40 to about 50. In some other embodiments, the boronic acid crosslinker has the following formula Ib:

wherein subscripts x, y and z are each independently from 1 to about 1000, preferably from 1 to about 75, more preferably from about 10 to about 50, such that x+y+z is from about 10

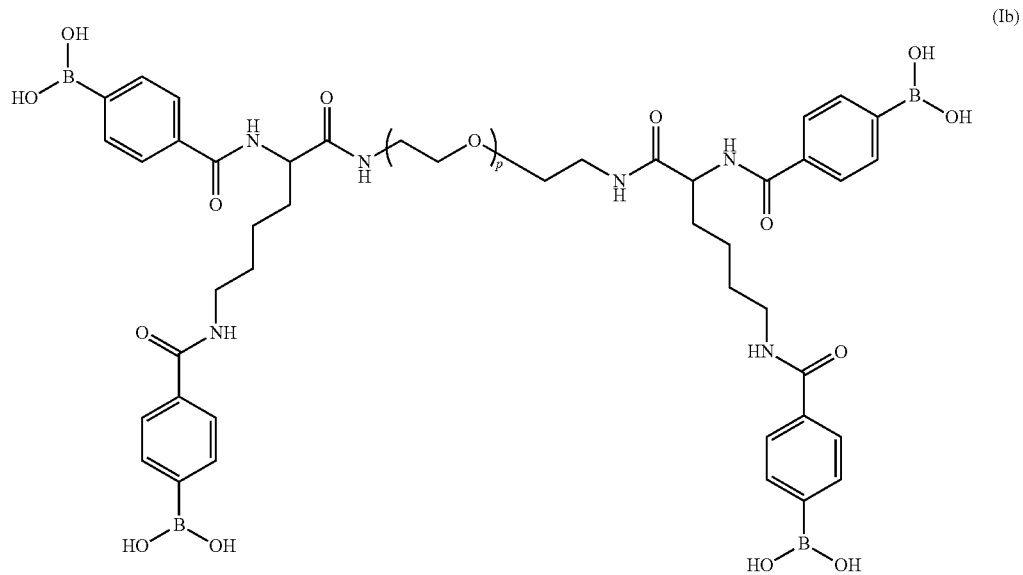

(Ib)

wherein subscript p is from about 10 to about 1000, preferably from about 10 to about 100, more preferably from about 40 to about 50. In still other embodiments, the boronic acid crosslinker has the following formula Ic:

to about 500, preferably from about 50 to about 150, more preferably from about 80 to about 90. In yet other embodiments, the boronic acid crosslinker has the following formula Id:

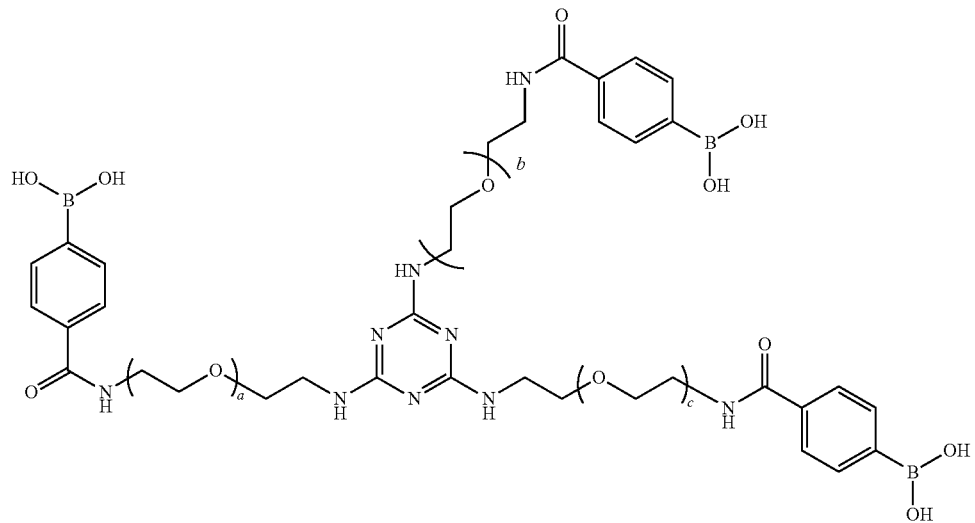
(Id)
wherein subscripts a, b and c are each independently from 1 to about 1000, preferably from about 10 to about 100, more preferably from about 40 to about 50, such that a+b+c is from about 50 to about 500, preferably from about 100 to about 200.
Other crosslinkers useful in the present invention include:
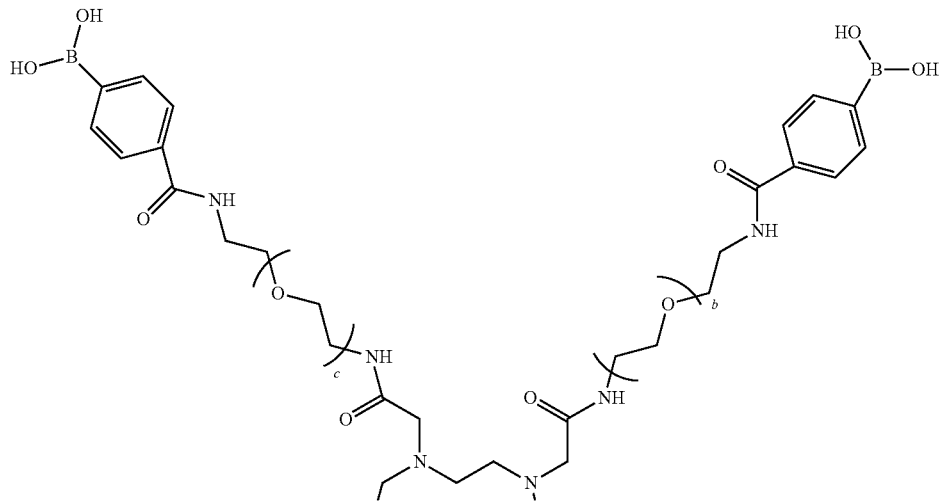

-continued

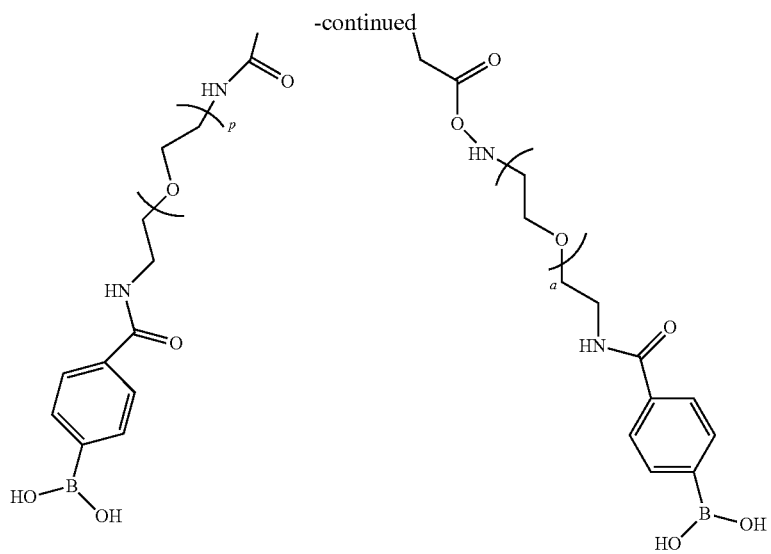

wherein subscripts a, b, c and d are each independently from 1 to about 1000, preferably from about 10 to about 100, more preferably from about 40 to about 50, such that a+b+c+d is from about 50 to about 500, preferably from about 100 to about 200.

In other embodiments, the process for preparing the cell adhesion matrix also includes contacting a molecular recognition element conjugate and the plurality of poly(vinyl alcohol) chains, wherein the molecular recognition element conjugate has at least one binding group, under conditions such that each binding group of the molecular recognition element conjugate becomes linked to one of the poly(vinyl alcohol) chains.

The molecular recognition element conjugate can be any species capable of recognizing or detecting a biological species, and include the molecular recognition element for performing the recognition or detection and a species for linking to the poly(vinyl alcohol) chain. For example, the molecular recognition element can be a cell adhesion ligand or a reporter substrate, among others. Cell adhesion ligands include, but are not limited to, RGD peptides, LXY3, MSE, HYD1, or LLP-2A. Reporter substrates include fluorescent substrates, such as fluorescence-quenched substrates of cell-secreted proteases. Other molecular recognition elements include bisphosphonates and G-protein-coupled receptor ligands. The molecular recognition element conjugate can also include releasable drugs.

TABLE 1

Scaffold-ligated molecular recognition elements

| Cell adhesion ligand | Integrin receptor type |
|---|---|
| RGD peptides | $\alpha_v\beta_3$, $\alpha_v\beta_5$, $\alpha_v\beta_{11}$, $\alpha_{IIb}\beta_3$, $\alpha_5\beta_1$ |
| LXY3 | $\alpha_3\beta_1$ |
| MSE, HYD1 | $\alpha_1$, $\alpha_5\beta_1$, $\alpha_6$ |
| LLP-2A | $\alpha_4\beta_1$ |

In other embodiments, the cell adhesion matrix of the present invention also includes an antibacterial ligand.

In some embodiments, the molecular recognition element conjugate has the following formula III:

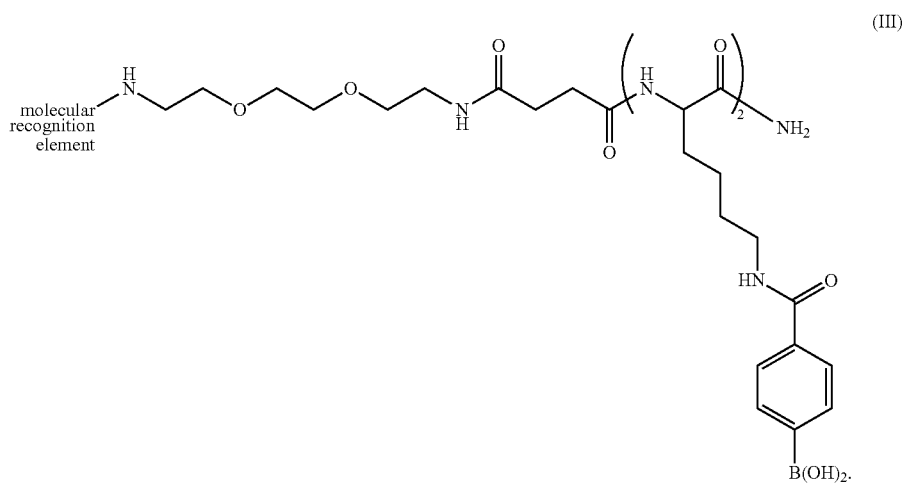

(III)

In some other embodiments, the molecular recognition element of the molecular recognition element conjugate is an LXY3, MSE, HYD1, LLP-2A, or RGD ligand. RGD ligands are integrin-binding arginine-glycine-aspartic acid sequences found in many ECM proteins. In still other embodiments, the poly(vinyl alcohol) chains are linked to at least one molecular recognition element. In yet other embodiments, there is more than one type of molecular recognition element linked to the poly(vinyl alcohol) chains.

Figure 10:
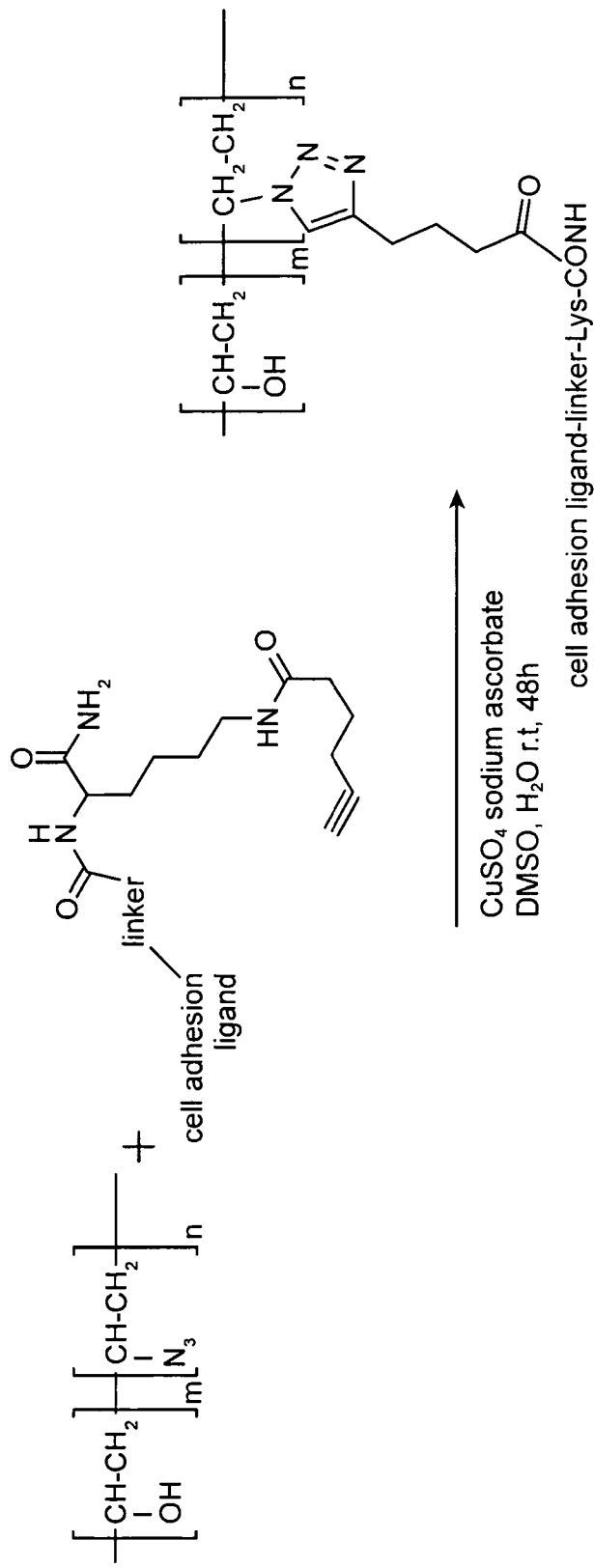
FIG. 10 shows the covalent "click" chemistry-mediated ligation of cell adhesion ligands to the PVA scaffold. Alkyne-functionalized ligands (via side chain reaction of an incorporated lysine with 5-hexynoic acid) are introduced to the PVA scaffold via reaction with azide-derivatized PVA (5-10% derivatization). Purified ligand-PVA conjugates are then crosslinked to form hydrogels.
Figure 11:
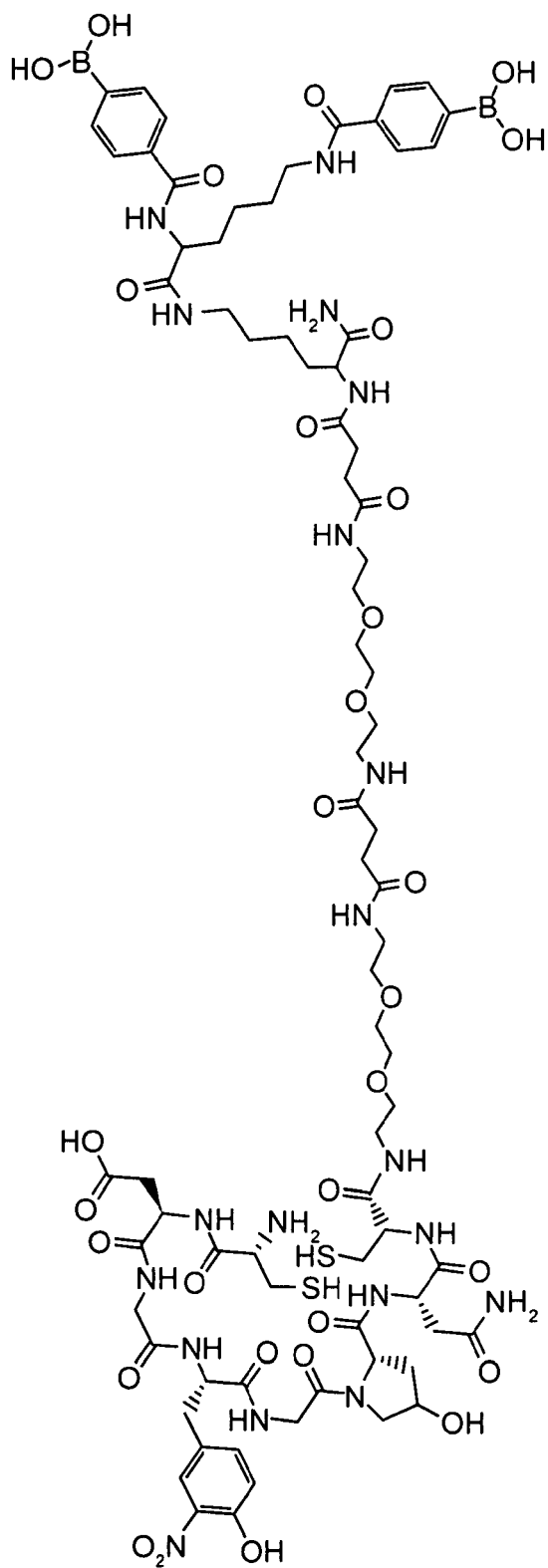
FIG. 11 shows the structure of molecular recognition element LXY3 with diboronic acid.

The molecular recognition element conjugate can also be linked to the PVA via "click chemistry" where the molecular recognition element conjugate is modified with an alkyne group and the PVA with an azide. Alternatively, the molecular recognition element is modified with the azide and the PVA with the alkyne. FIG. 10 shows one example of linking the molecular recognition element to the PVA via click chemistry.

The present invention also provides a cell adhesion matrix including a carboxy phenyl boronic acid crosslinker having at least two carboxy phenyl boronic acids linked by a Linker having a biocompatible polymer. The cell adhesion matrix also includes a plurality of poly(vinyl alcohol) chains, wherein each boronic acid is linked to two adjacent hydroxy groups of one of the plurality of poly(vinyl alcohol) chains. In other embodiments, the cell adhesion matrix can include a molecular recognition element conjugate (as described within). In some other embodiments, the cell adhesion matrix includes a cell.

The present invention also provides a method for preparing a cell adhesion matrix. The method includes contacting a plurality of poly(vinyl alcohol) chains and a carboxy phenyl boronic acid crosslinker having at least two carboxy phenyl boronic acids in a mixture, under conditions such that each boronic acid becomes linked to two adjacent hydroxy groups of one of the plurality of poly(vinyl alcohol) chains, thereby preparing the cell adhesion matrix. The mixture can also include a plurality of cells.

In some embodiments, the method also includes contacting a molecular recognition element conjugate and the plurality of poly(vinyl alcohol) chains in a mixture, wherein the molecular recognition element conjugate has at least one binding group, under conditions such that each binding group of the molecular recognition element conjugate becomes linked to one of the poly(vinyl alcohol) chains. In some embodiments, the binding group can be a carboxy phenyl boronic acid. In other embodiments, the binding group can an alkyne or azide.

The present invention also provides a cell adhesion matrix prepared by the process including contacting a molecular recognition element conjugate of formula (III):

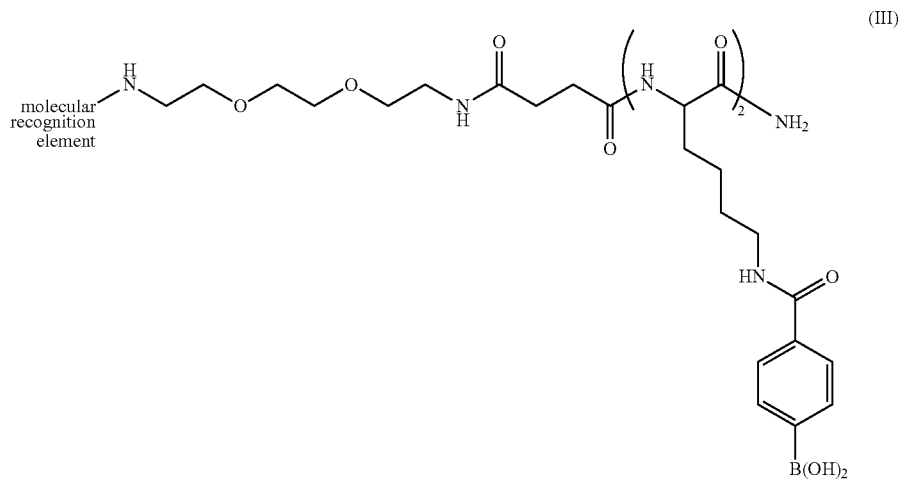

wherein the molecular recognition element is LXY3, MSE, HYD1, LLP-2A, or RGD ligand, and a plurality of poly(vinyl alcohol) chains of formula (II):

wherein subscript n is from about 10 to about 5000. The contacting is performed at a pH of about 7.4 such that each boronic acid of the molecular recognition element conjugate becomes linked to two adjacent hydroxy groups of one of the poly(vinyl alcohol) chains to form a plurality of modified poly(vinyl alcohol) chains. The method also includes contacting the plurality of modified poly(vinyl alcohol) chains and a carboxy phenyl boronic acid crosslinker of formula Ia, formula Ib, formula Ic, of formula Id, at a pH of about 7.4 such that each boronic acid becomes linked to two adjacent hydroxy groups of one of the plurality of modified poly(vinyl alcohol) chains.

The present invention also includes a method of de-gelling the cell adhesion matrix of the present invention, by contacting the cell adhesion matrix of the present invention with a de-gelling agent. The de-gelling agent can be any suitable agent capable of replacing the adjacent hydroxy groups of the poly(vinyl alcohol) chains in the boronic esters. The de-gelling agent can be any cis-diol compound such as a sugar. Cis-diol compounds useful as the de-gelling agent include, but are not limited to, fructose, sorbitol, glucose, mannitol, and dextrose, among others.

The cell adhesion matrix of the present invention is useful for a variety of therapeutic applications, such as (i) treatment of neuronal damages and spinal cord damages by local administration of pluripotent or neurogenic stem cells embedded in cell adhesion matrix at the injured site, (ii) the use of the cell adhesion matrix as scaffold to build tissues and organs (e.g. blood vessels), (iii) injection of cell adhesion matrix at the surgical site to aid wound healing, (iv) injection of cell adhesion matrix embedded with antibiotics at sites of infections, (v) injection of cell adhesion matrix with appropriate platelet adhesion ligands that promote coagulation to stop internal bleeding, and (vi) application of cell adhesion matrix with appropriate platelet adhesion ligands to bleed sites. Moreover, the cell adhesion matrix of the present invention can be used for skin grafting, either ex vivo or in vivo. In some embodiments, the present invention provides a method of treating a disease or condition by using the cell adhesion matrix to administer cells to a specific location, tissue, or organ of a subject in need thereof.

III. EXAMPLES

Example 1

Figure 8:
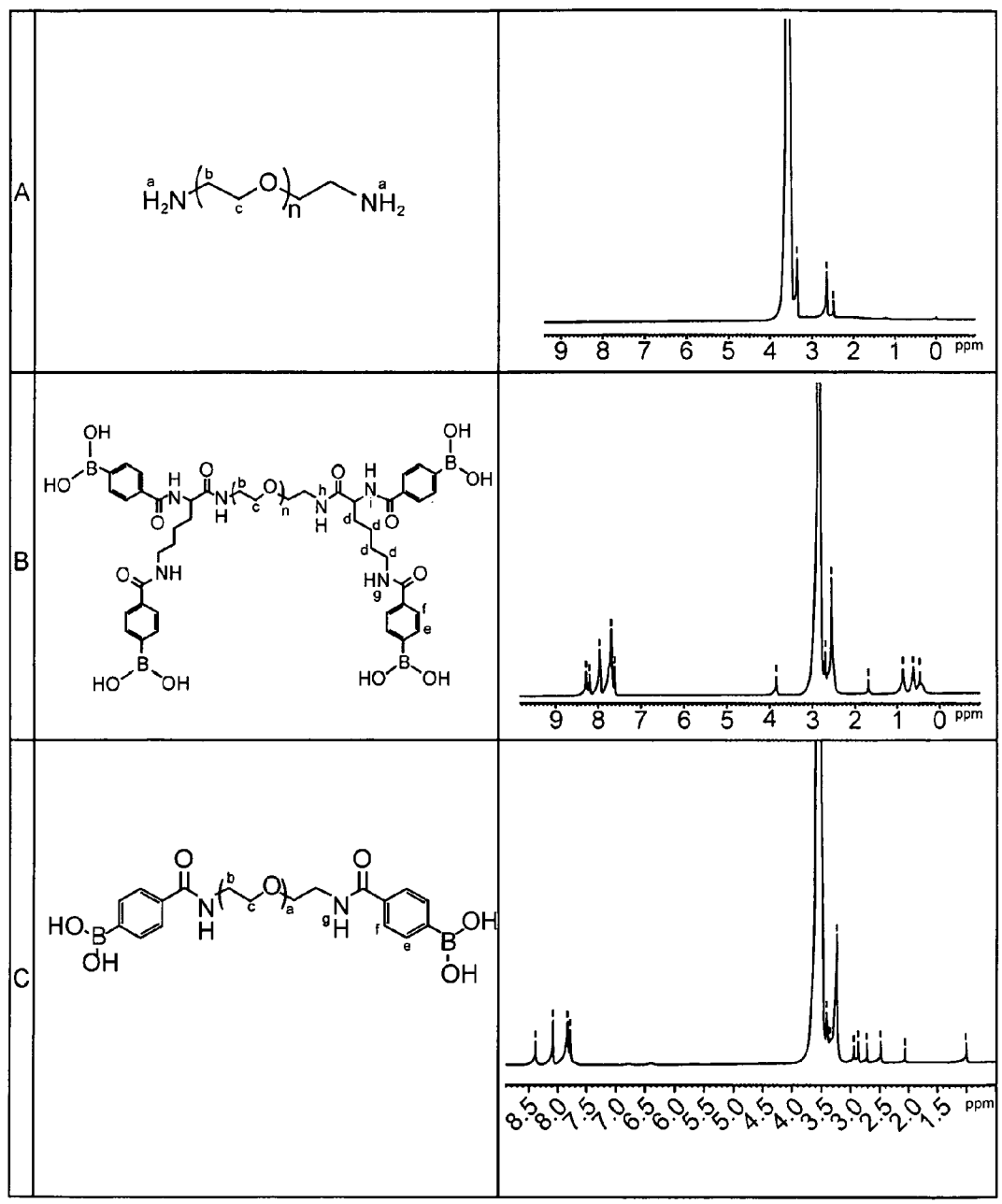
FIGS. 8a, 8b and 8c show $^1$H NMR characterization (in $d_6$-DMSO) of boronic-acid derivatized crosslinkers. Shift of free amine protons ($\delta$ 2.5 ppm) in unmodified bis-amino PEG (A) to amide protons ($\delta$ 7.8 ppm) in the boronic acid-derivatized PEG polymers (B and C) is observed. In B) the appearance of a (4.4 ppm) and $\beta,\gamma,\delta,\epsilon$ (triplet $\delta$ 1.4-1.7 ppm) methylene protons from the lysine side-chain, and aromatic protons from the phenyl ring (doublet, $\delta$ 8.35 ppm), confirmed the structure of the PEG-tetraboronic acid crosslinker. PEG-diboronic acid (C) is also characterized by the appearance of amide and aromatic protons ($\delta$ 7.8-8.5 ppm).
Figure 9:
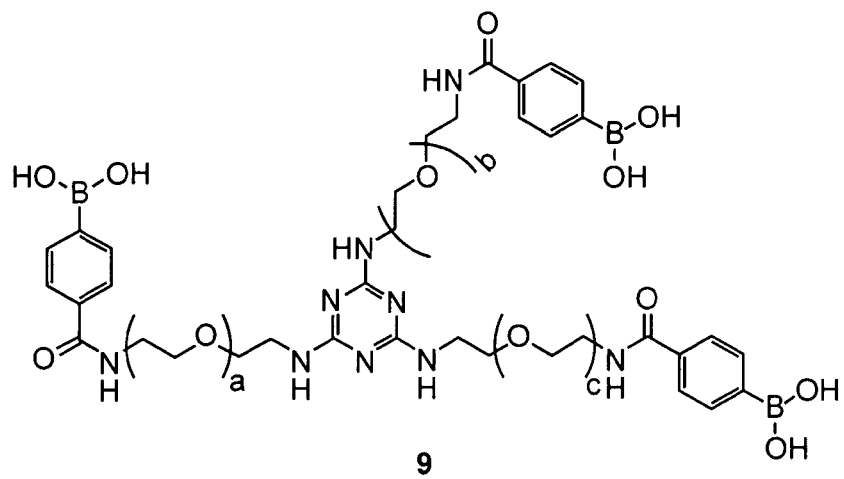
FIG. 9 shows additional branched PEG-boronic acid crosslinkers, including a hydrophilic triboronic acid crosslinker 9 comprised of three cyanuric-linked PEG-boronic acids (a ~45). In similar fashion, the compounds ethylenediaminetetraacetic acid (EDTA) and diethylenetriaminepentaacetate (DTPA) can be utilized as branching groups in the syntheses of hydrophilic tetravalent and pentavalent PEG-boronic acid crosslinkers.
Figure 9:
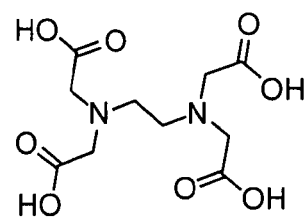
Figure 9:
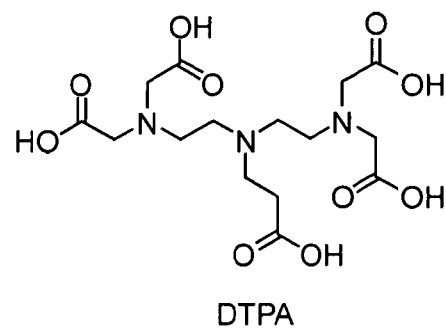

Preparation of Bis-Amino Carboxy Phenyl Boronic Acid (PEG-Diboronic Acid (dbPEG), 4)

dbPEG was prepared by reacting 4-carboxycarboxy phenyl boronic acid (4-CPBA) with bis-amino PEG ($M_w$ 2000 Da, from Rapp Polymere GmbH, Tübingen, Germany) using standard HOBT/DIC coupling chemistry in DMF overnight. The product (4) was isolated by precipitation using 10-fold excess of cold ethyl ether, and dialyzed repeatedly against deionized, distilled water (dd$H_2O$). $^1$H NMR characterization (in $d_6$-DMSO) of boronic-acid derivatized crosslinkers can be found in FIG. 8. FIG. 8 shows the shift of free amine protons (δ 2.5 ppm) in unmodified bis-amino PEG (8A) to amide protons (δ 7.8 ppm) in the boronic acid-derivatized PEG polymer (FIG. 8C) is observed. The PEG-diboronic acid in FIG. 8C is also characterized by the appearance of amide and aromatic protons (δ 7.8-8.5 ppm).

Example 2

Bis-(amino-lysine-dicarboxyphenylboronic acid)-PEG (PEG-tetraboronic acid, 6)

PEG-tetraboronic acid was prepared by sequential coupling of fmoc-Lysine(fmoc)-OH, and 4-carboxycarboxy phenyl boronic acid, to bis-amino PEG using standard HOBT/DIC chemistry in DMF. Polymer product after each coupling step was precipitated using 10-fold excess of cold ethyl ether, and dialyzed repeatedly against dd$H_2O$. FIG. 8 shows the shift of free amine protons (δ 2.5 ppm) in unmodified bis-amino PEG (8A) to amide protons (δ 7.8 ppm) in the boronic acid-derivatized PEG polymers (8B and 8C) is observed. In FIG. 8B, the appearance of α (4.4 ppm) and β,γ,δ,ε (triplet δ 1.4-1.7 ppm) methylene protons from the lysine side-chain, and aromatic protons from the phenyl ring (doublet, δ 8.35 ppm), confirmed the structure of the PEG-tetraboronic acid crosslinker.

Example 3

Polypropyletheramine-tricarboxy phenyl boronic acid (PPO-triboronic acid, 5)

PPO-triboronic acid was prepared by boronic acid-modification of a Jeffamine T-5000 polyetheramine (polypropylene oxide triamine polymer, Huntsman Corporation). 4-carboxycarboxy phenyl boronic acid was coupled to the triamine polymer overnight in DMF using standard HOBT/DIC chemistry. The final product was purified on a desalting gel filtration column.

Example 4

Preparation of Cell Adhesion Ligand LXY3

Cell adhesion ligands were prepared as previously reported (Nat Chem Biol 2005, 2:381-9; J Med Chem 2009, 52:126-33) on Rink amide MBHA resin (Rapp Polymere) using standard peptide solid phase 9-fluorenylmethoxycarbonyl (Fmoc) and HOBt/DIC chemistry (Int. J. Pept. Protein Res. 1990, 35, 161-214) and completion of each coupling step was monitored using the ninhydrin test. The protected amino acids and coupling reagents were purchased from NovaBiochem (San Diego, Calif.) or GL Biochem (Shanghai, China). The hydrophilic ethyleneglycol based linker, Ebes, was synthesized as reported previously (Bioorg Med Chem Lett 2004; 14:161-5). In synthesis of the molecular recognition element conjugate, solid support-coupling of Ebes linker and two lysine residues preceded assembly of the cell adhesion ligand sequence (LXY3 as an example), and the lysines were subsequently modified via side-chain/epsilon amine condensation with 4-carboxycarboxy phenyl boronic acid, in order to facilitate boronic acid-polyol ligation of the ligands to the PVA scaffold. The conjugates were cleaved from solid support using a trifluoroacetic acid (TFA) mixture containing 82.5% TFA:5% phenol:5% thioanisole:5% $H_2O$:2.5% triisopropylsilane, followed by precipitation in cold ether. Cyclic peptide ligands were obtained via activated charcoal-assisted disulfide bond formation of crude peptides in aqueous $NH_4HCO_3$ buffer (J. Pept. Res. 1998, 51, 365-369). The molecular recognition conjugates were finally purified by preparative reverse-phase high performance liquid chromatography (RP-HPLC), and lyophilized to powdered solids. Molecular masses were confirmed by MALDI mass spectrometry.

Example 5

Preparation of Molecular Recognition Element Conjugate Containing an Alkyne and LXY3

Alkyne-functionalized ligands (LXY3 as an example) were synthesized following the general procedure in example 4, with the following modifications: the Ebes linker and a single lysine residue were incorporated before the ligand sequence, and the lysine side-chain amine was reacted with 5-hexynoic acid to facilitate subsequent covalent ligation of the ligand to an azido-derivatized PVA scaffold via Cu(I)-catalyzed alkyne-azide cycloaddition ("click chemistry"). Cleavage, precipitation and purification steps were performed as described above.

Example 6

Preparation of PVA/PEG-boronic Hydrogels

The two-step preparation of 100 μL of a hydrogel containing 91 wt % water, 4.5 wt % PVA, 4.5 wt % dbPEG, and 50 μg/mL of LXY3 (an $α_3β_1$ integrin-binding ligand) is described.

First, a PVA-ligand conjugate is prepared as follows: 45 μL of a PVA solution (10 wt % dissolved in cell line-specific complete culture medium and filter-sterilized via a 0.22 μm pore syringe) is mixed with 5 μL of LXY3 solution (1 mg/mL, dissolved in culture medium and filtered), and 20 μL of culture medium. This mixture is incubated at 37° C. for 10 min (or at 25° C. for 20 min) to allow for complexation of boronic acid groups on the cell adhesion ligands with polyhydroxyls on PVA. For cell encapsulation assays, during this step, an aliquoted cell pellet is re-suspended to single cells in the PVA-ligand mixture after the incubation period.

Figure 12:
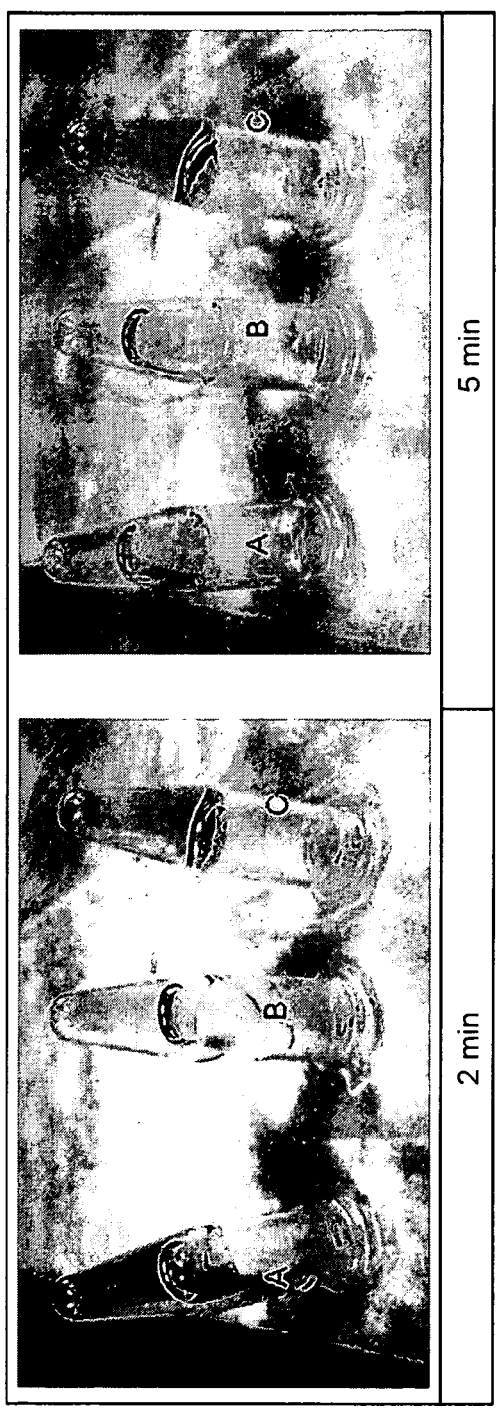
FIG. 12 shows hydrogel formation in the presence of boronic acid crosslinkers-gels formed using PVA and diboronic acid-PEG crosslinker in 1:1 ratio (wt/wt) of both polymers and 9 wt % total polymer concentration (vial C) remain stable at 37° C. as demonstrated using a vial inversion test. Hydrogels prepared using lower crosslinker concentration, 1:2 and 1:4 dbPEG/PVA (vials B and A, with 7% and 5.5% total polymer concentration wt/wt, respectively) turn into viscous fluids after a few minutes at 37° C.
Figure 13:
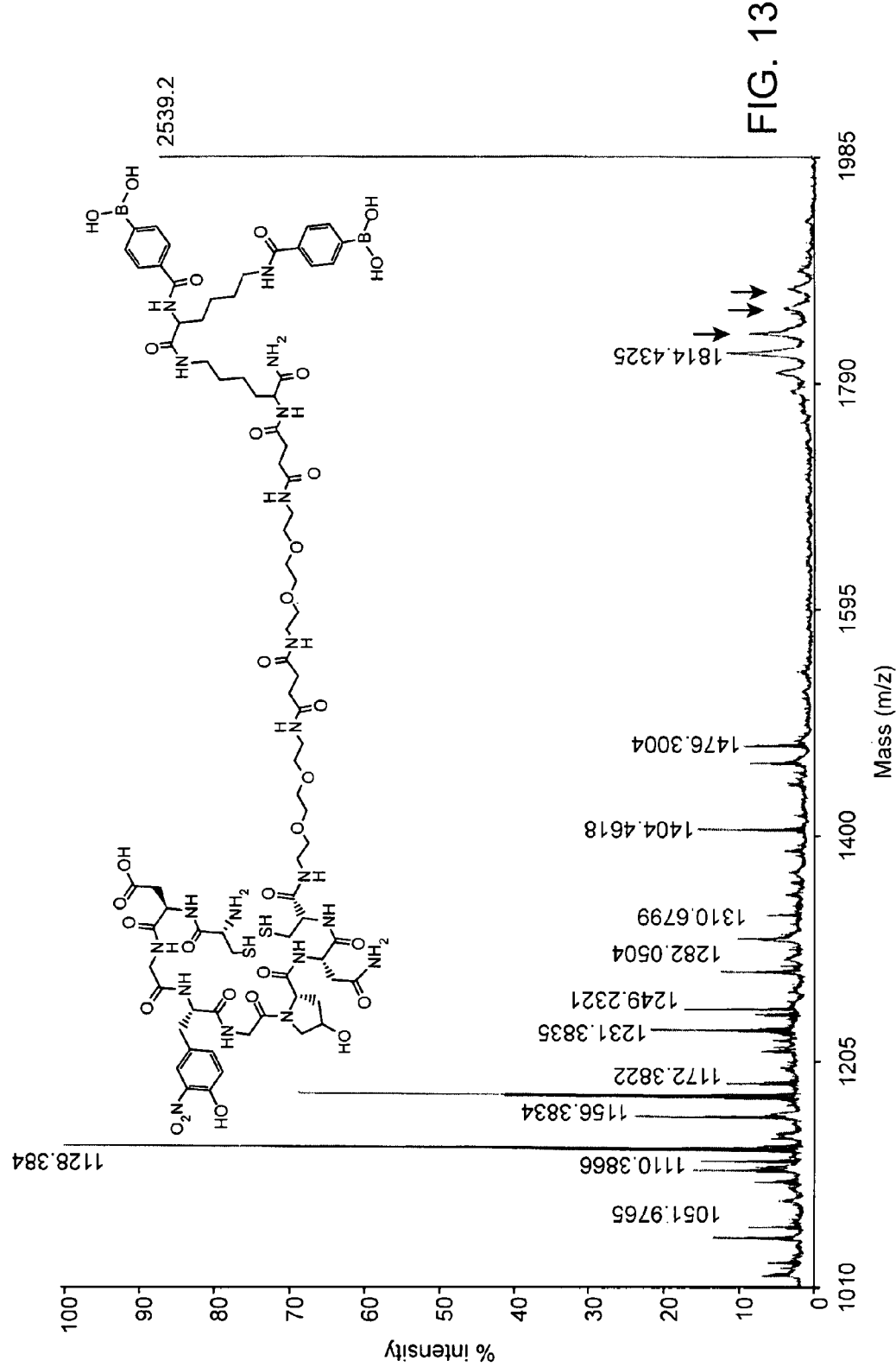
FIG. 13 shows MALDI spectrum of molecular recognition element LXY3 with diboronic acid (prepared in example 4). Calculated mass was 1899.79, identified observed masses were 1882.7 m/z and 1864.5 m/z, corresponding to the protonated-dehydration ion products $(M+H-H_2O)^+$ and $(M+H-2H_2O)^+$ respectively.

30 μL PEG-diboronic acid solution (15 wt % dissolved in culture medium, filtered) is subsequently added to a well containing the PVA-ligand scaffold mixture and crosslinking and hydrogel formation occurs rapidly within 1-2 minutes. The mixture can be stirred gently using a pipette tip until the gel hardens. See FIG. 12 showing tube inversion test for this matrix.

Example 7

Preparation of PVA/PEG-boronic Hydrogels

Following the procedure in Example 6 using the 30 μL PEG-diboronic acid solution (15 wt % dissolved in culture medium, filtered) is subsequently added to a well containing the PVA-ligand scaffold mixture and crosslinking and hydrogel formation occurs rapidly within 1-2 minutes. The mixture can be stirred gently using a pipette tip until the gel hardens.

Example 8

Dissolution of Hydrogels

Hydrogels were degraded by incubation at 37° C. with 2-fold volumes of serial concentrations of fructose dissolved in culture medium, and time required for complete dissolution of the gel were measured. For 100 μL of the PVA-dbPEG hydrogel described above, 200 μL of 100 mM fructose and an incubation time of 20 minutes were sufficient for complete dissolution of the hydrogel.

Example 9

Cell Culture

All cell types used were purchased from American Type Culture Collection (ATCC) and propagated in ATCC-recommended complete culture media. 3D cell culture in the hydrogels was performed using either an encapsulation or overlay method. All hydrogel scaffolding materials were dissolved in complete growth medium, and filtered through a 0.22 μm syringe. In encapsulation assays, a cell pellet was mixed gently with the PVA-ligand conjugate solution, followed by crosslinking of the scaffold to yield cells encapsulated in situ within the hydrogel matrix. Cells were encapsulated at a density of 30,000 cells/100 μL of hydrogel in 96 well plates.

In the overlay method, cells suspended in appropriate culture medium were seeded at a density of ~15,000 cells/cm$^2$ atop a pre-formed hydrogel. For tube formation assays, the seeded cell density was doubled. With both methods, the hydrogel was finally topped with culture medium containing 4.5 wt % of the crosslinking polymer to prevent dissolution of the hydrogel. 3D culture in lrECM was done using both encapsulation and overlay assay methods and corresponding cell densities in 100% Matrigel (BD Biosciences) topped with culture medium. For overlay cultures, seeded cells were topped with culture medium supplemented with 10% Matrigel. All 3D cultures were maintained for 10-20 days, with media renewal every 2-3 days.

Example 10

Extraction of Cells from 3D Culture, Immunostaining

After 8-10 days in 3D culture, cells were fixed in situ using 4% formaldehyde (4% paraformaldehyde dissolved in PBS, pH 7.4), followed by dissolution of the hydrogel matrix using fructose (100 mM fructose in PBS, incubated for 20 minutes). Cell colonies were collected on a slide via cytospinning, and incubated with primary and Alexa-flour conjugated secondary antibodies (Cell Signaling, Invitrogen, respectively) according to general immunofluorescence protocols.

Example 11

Preparation of Cyanuric PEG Boronic Acid Crosslinker (9)

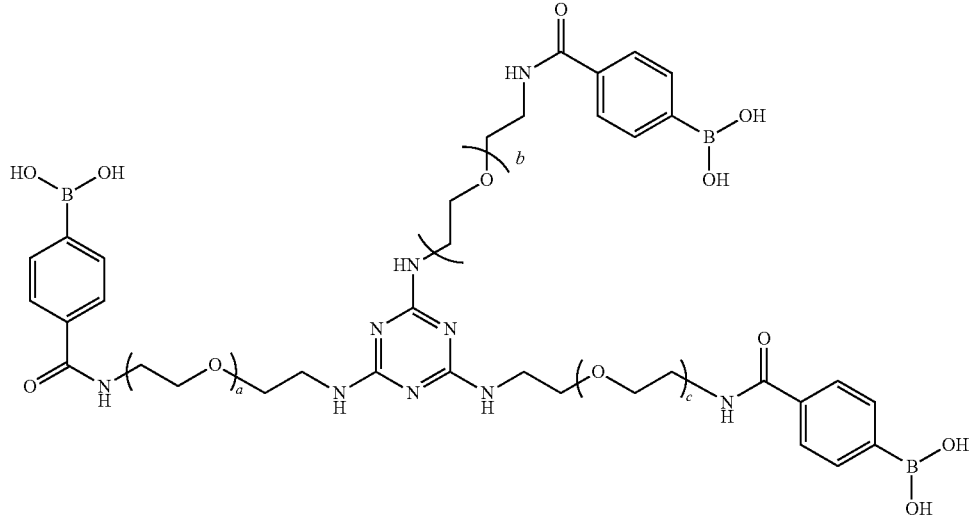

Cyanuric-tri-amino PEG carboxyphenyl boronic acid (PEG-triboronic acid (tri-b-PEG)) was prepared by reacting cyanuric chloride with an excess of T-Boc-amino PEG-amine ($M_w$ 2000 Da, from Jenkem USA) in dichloromethane. The Boc protecting group was removed using trifluoroacetic acid, and the resulting product was reacted with 4-carboxyphenyl boronic acid (4-CPBA) using standard HOBT/DIC coupling chemistry in DMF overnight. The product 9 was isolated by precipitation using 10-fold excess of cold ethyl ether, and purified on a sephadex G10 column using deionized, distilled water (dd$H_2O$) as an eluent.

Example 12

Three-Dimensional Culture of Pluripotent Stem Cells

The goal of this study was to investigate the fate of pluripotent stem cells ensheathed in a novel 3D hydrogel matrix comprised of a crosslinked polymeric meshwork with tethered integrin-binding ligands identified using the one-bead-one-compound method.

Polymeric hydrogels comprised of polyvinyl alcohol (PVA), crosslinked via boronic acid esterification in aqueous cell culture media at room temperature or 37° C. (using multivalent boronic acid-modified polyethylene glycol (PEG) amine, also known as "PEG crosslinker" as described previously). The cell adhesion ligands LLP2A, LXY3, HYD-1, previously identified using the one-bead-one-compound (OBOC) method, and shown to bind $\alpha_4\beta_1$, $\alpha_3\beta_1$, $\alpha_6\beta_1$, respectively, and LXW7 shown to interact with $\alpha v\beta 5$ and $\alpha 5\beta 1$, were functionalized synthetically with carboxyphenyl boronic acid, and tethered to PVA in aqueous solution via boronic acid esterification prior to the crosslinking step. Hydrogels with final composition 4.5% w/w PVA, 5.8% w/w PEG crosslinker, 89.7% w/v buffered aqueous tissue culture medium (either basal medium or complete stem cell culture mTeSR medium). Synthetic ligand concentration in the hydrogels were as follows: 0.92 βM LLP2A, 30 µg/mL HYD-1, 18.9 µg/mL LXW7, 18.9 µg/mL LXY3.

Human induced pluripotent stem cells (iPSCs, System Biosciences), and human embryonic stem cells (hESC H9 cells, UC Davis Stem Cell Core) were first cultured as embryoid bodies on either reduced growth factor Matrigel-coated plates or on irradiated human foreskin fibroblasts (System Biosciences), trypsinized to single cell suspension at near-confluence, and re-cultured in synthetic hydrogels using the overlay method. Briefly, cells were seeded singly in culture medium atop of the pre-gelled matrix, allowed to attach, and overlaid with a dilute solution of PEG crosslinker in either aqueous stem cell base culture medium (no added supplements), or complete stem cell culture medium (mTESR-aqueous culture medium supplemented in full with cell growth factors). Cells were maintained in gels for 3 to 13 days, and fed by aspirating and replacing overlaid spent media. At the end of culture period, cells were fixed in situ using 4% formaldehyde, extracted from the gels after dissolution of gels using 100 mM dopamine in PBS (or 100 mM fructose in PBS), cytospun to slides, stained using indirect immunofluorescence, and analyzed via confocal microscopy.

Figure 14:
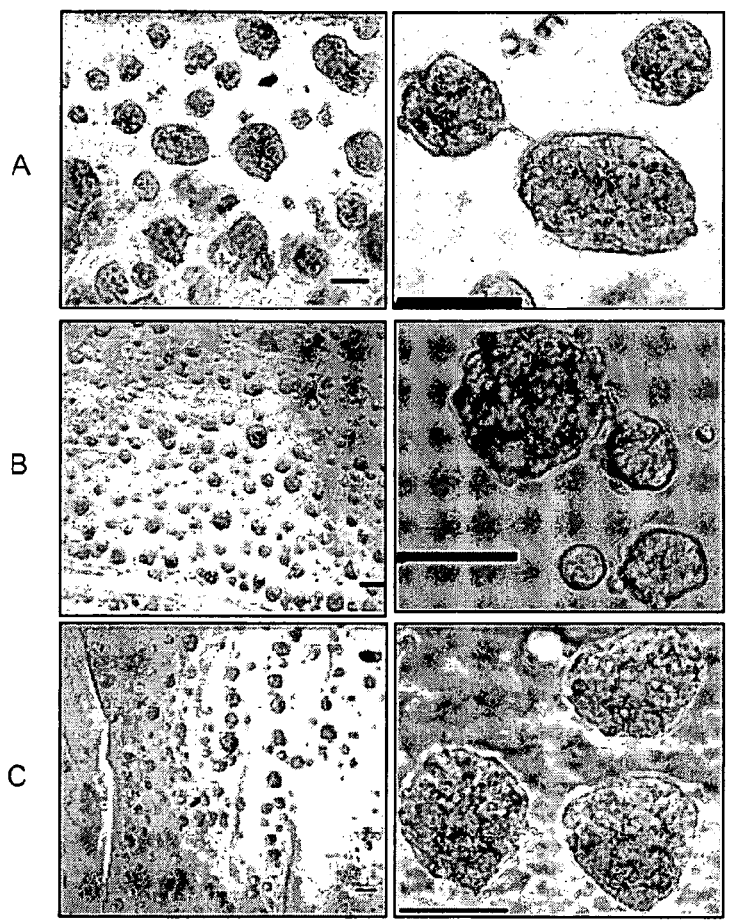
FIG. 14 shows phase contrast micrographs of iPSCs in 3D hydrogel culture, day 6. Embryoid bodies were formed in ligand-free hydrogels containing complete culture medium with growth factor supplements (A), "naked hydrogels" containing basal medium without factors or tethered synthetic integrin ligands (B), integrin ligand hydrogels containing basal medium with synthetic polymer-tethered integrin-binding ligands but no growth factors (C). Scale bars measure 100 µm.

Fate of iPSCs in 3D culture—maintenance of cell viability and formation of spheroid cell clusters (embryoid bodies) in 3D culture. Induced pluripotent stem cells cultured in three dimensions (3D) in polymeric hydrogels formed clusters of cells reminiscent of embryoid bodies (EBs) after 24 h in culture, both in the presence and absence of growth factor-supplemented medium (FIG. 14, C), and with or without polymer-tethered integrin ligands present, highlighting the suitability of the gel meshwork and physical properties for embryoid body morphogenesis. Embryoid bodies varied in size and shape, with the spheroid being the most predominant structure. Formed embryoid bodies grew larger in size with additional days in culture, reaching an average diameter of 85 µm by day 7 (N=150). Cells remained viable (cell tracker experiments, not shown) for the entire duration of the culture period (up to 13 days).

Figure 15:
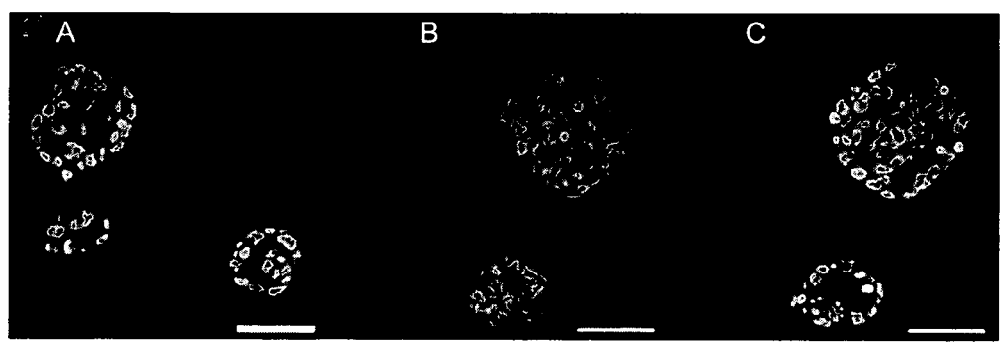
FIG. 15 shows confocal microscopic images of iPSCs cultured in basal medium hydrogels and harvested after day 7. Single optical equatorial sections (A, C) 1 µm thick, in the z-axis through the center of the specimen shows spheroids with central cavitation surrounded by a single layer of cells. Larger spheroids (topmost in image A, and upper spheroid in image C) appeared as incomplete cavities, with a number of cells still present in the lumen. B is an orthogonal projection of all confocal z-sections (22 total) of an image, while C is the corresponding equatorial optical section in the z-axis through this image. Scale bars measure 50 µm.
Figure 16:
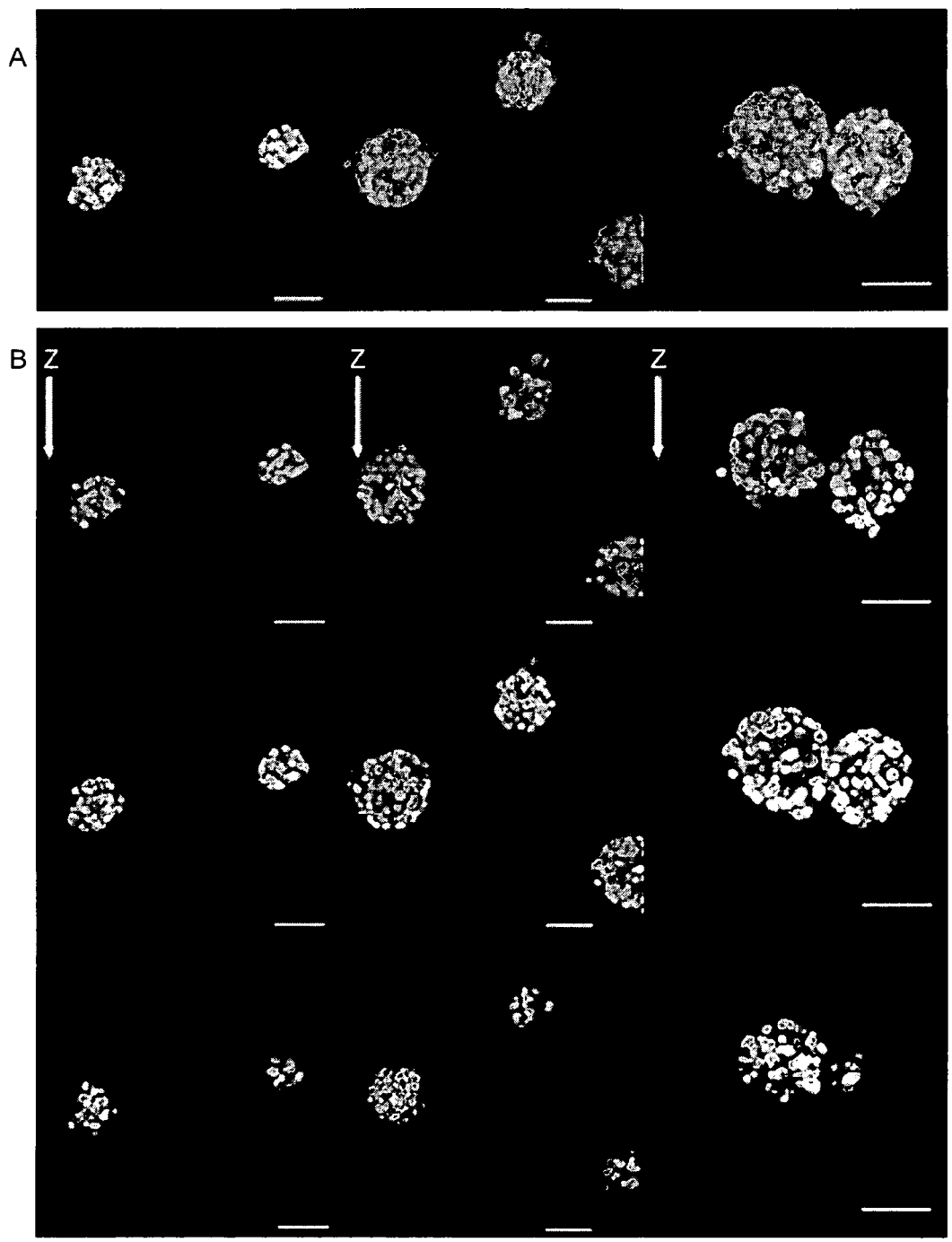
FIG. 16 shows confocal micrographs of DAPI-stained iPSCs cultured in complete medium hydrogels and harvested on day 7. Orthogonal projection of z-sections to a single plane (A) shows the total number of cells within each spheroid. Progression through each z-stacked image (B, in the direction of the arrow, z-axis) shows the uppermost part of the spheroids as the first 1 µm section in the z-axis (uppermost images), the center of the spheroids with no discernible lumen (middle images), and the bottom of the spheroids (bottom images). Spheroids of various sizes are shown for comparison in middle and right column. Scale bars in A and B measure 50 µm.
Figure 17:
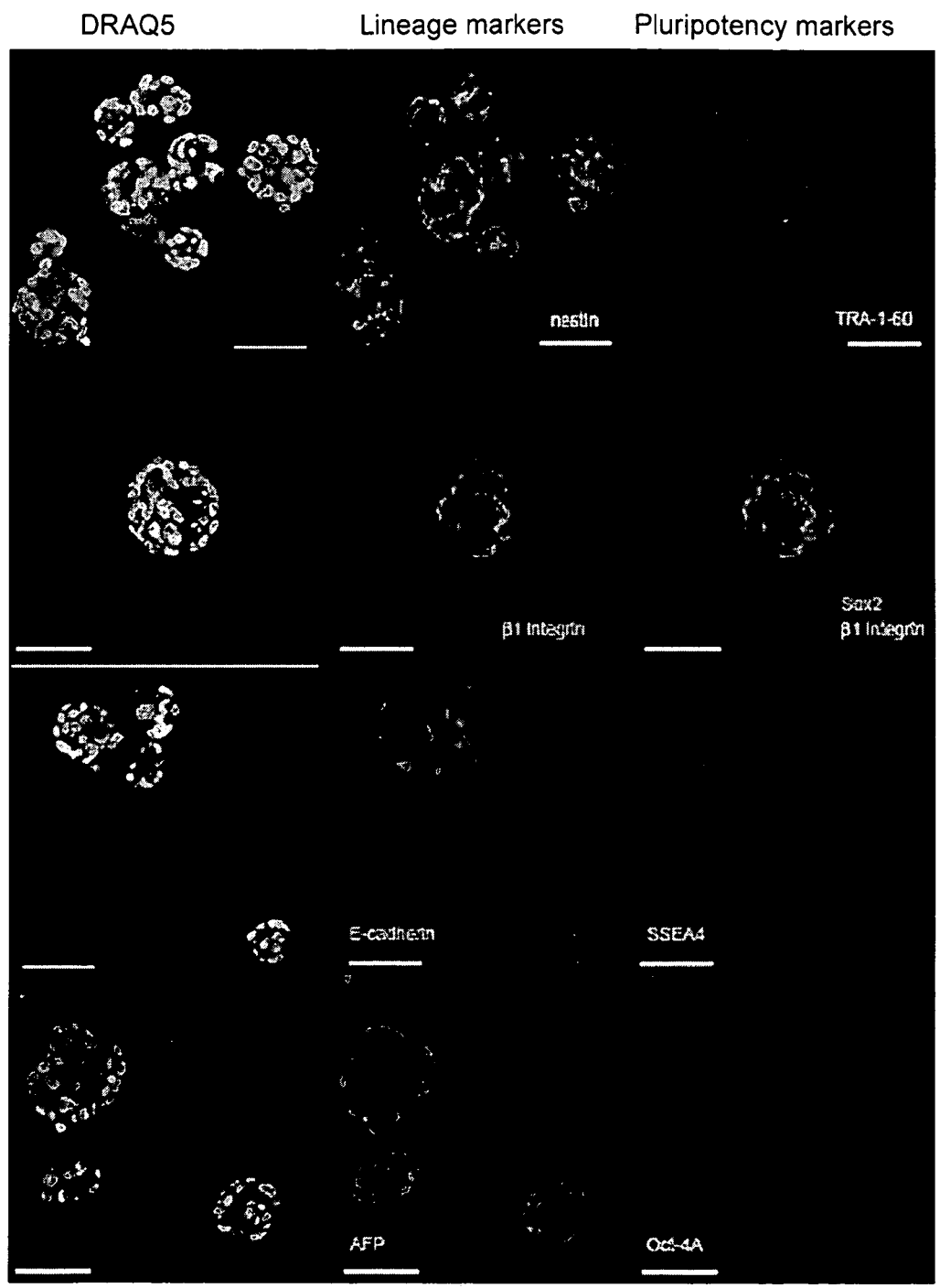
FIG. 17 shows confocal micrograph sections of iPSCs cultured in integrin ligand hydrogels and harvested after 7 days in culture. Z-section is through the center of specimen, and DRAQ5 nuclear stain showing central lumen present within the section in most spheroids (left column). Spheroids stained positive for multilineage markers (middle column), including ectodermal nestin (top image, middle column), $\beta1$ integrin non-specific endoderm and mesoderm marker (2$^{nd}$ image in column), E-cadherin, a non-specific endodermal marker also expressed in the early embryo (third image, middle column), and endodermal alpha-fetoprotein (middle column, bottom image). Embryoid bodies also stained positive for pluripotency markers cytoplasmic TRA-1-60, nuclear Sox2, cytoplasmic SSEA4, and Oct4 (right column, top, second, third and bottom images, respectively), although there is a high amount of background staining due to challenges presented by immunofluorescence and confocal imaging of thick specimens. DRAQ5 pseudocolor in middle and right column images. All scale bars measure 50 µm.

Effect of culture medium supplements on iPSCs in 3D culture. To investigate the effect of culture medium components on iPSCs in 3D culture, cells were seeded atop integrin ligand-free hydrogels prepared in either basal stem cell medium, or complete serum-free, growth factor-supplemented stem cell culture medium, and maintained in 3D culture for 7 days. iPSCs grown in basal medium hydrogels formed hollow spheroids with marked central cavitation reminiscent of lumina of epithelial gland acini (FIG. 15). In smaller spheroids, central lumina were surrounded by a single layer of cells, while larger spheroids tended towards incomplete cavitation, with a number of cells still present within the lumen (FIG. 15A, C). This finding was in stark contrast to the observed non-hollow structures formed by these cells in hydrogels prepared using growth factor-supplemented culture medium (FIG. 16). Here, cells were contained within the full thickness of both small and larger spheroids (FIG. 16B). Luminal clearing thus appeared to be rescued in the presence of growth factors and other cytokines present within the complete medium hydrogel. Thus the influence of the culture medium on iPSC fate in 3D culture is most pronounced in cells within the center of the embryoid bodies, where they are either rescued or delayed from undergoing cell death.

iPSCs in integrin ligand matrices differentiate into all three germ layers. The influence of cell-matrix (biomaterial) interactions on iPSC fate was probed in 3D culture of iPSCs seeded atop hydrogels comprised of polymer-tethered integrin-binding molecular recognition elements in the absence of growth factors or other culture supplements. Here, the sole biochemical cell signaling components are the integrin-binding ligands. Cells formed spheroidal structures with central lumina and stained positively for expression of markers of all three germ layers, including the ectodermal nestin, β1 integrin found in both mesoderm and endoderm, and c-Kit (mesoderm, data not shown), with residual but weak expression of pluripotency markers Sox2 and TRA-1-60 (FIG. 17).

Example 13

Three-Dimensional Culture of Mammary Epithelial Cells (MECs)

Figure 18:
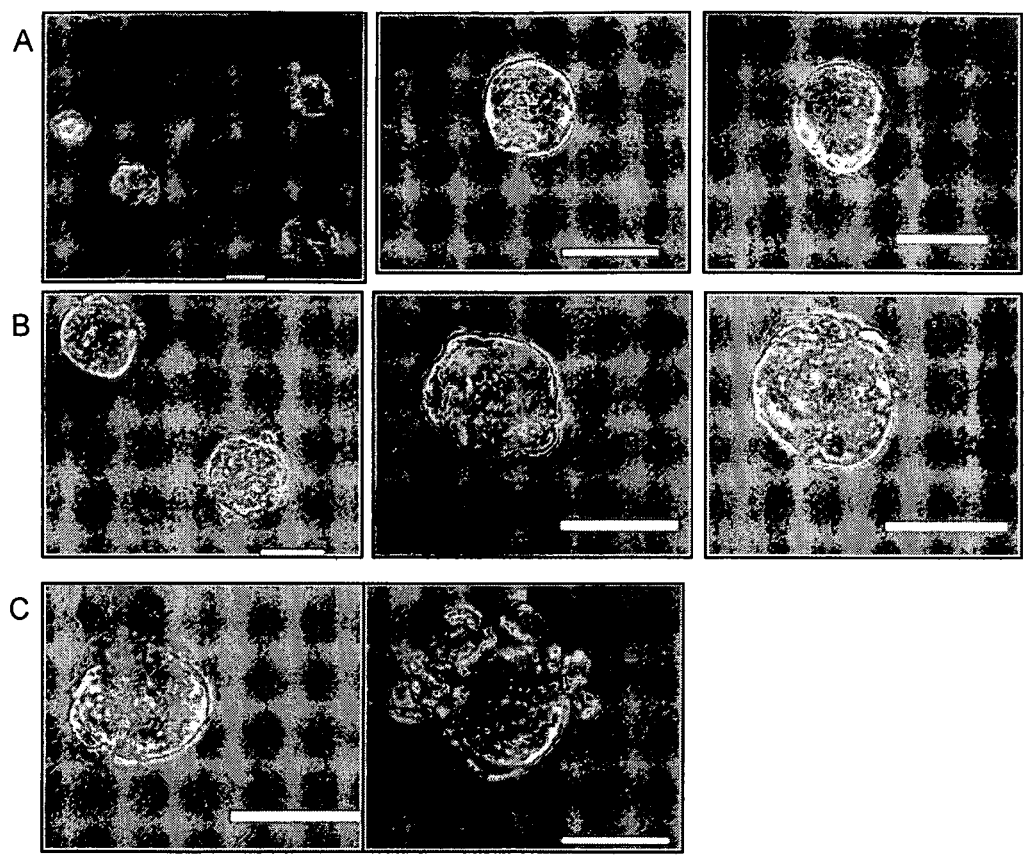
FIG. 18 shows phase contrast micrographs of MCF 10A on day 13 of culture. Cells were cultured in overlay assay on top of gel and imaged on day 13. Scale bars measure 50 µm.

MECs form multicellular spheroids in artificial hydrogel matrices. MCF 10A cells formed multicellular spheroids 3 days after being seeded atop polymeric hydrogels (FIG. 18). Observed morphical patterns of cultured cells included round, smooth spheroids (FIG. 18A) and spheroids with identifiably flattened or rounded peripheral cells, (FIG. 18B). Clusters of cells associated with the spheroids were also seen (FIG. 18C), and finally, a few number of cells in culture remained single, round and unassociated with any spheroids (not shown). The multicellular spheroids increased in size with additional days in 3D culture, with spheroids roughly around 80 µm by day 13.

Figure 19:
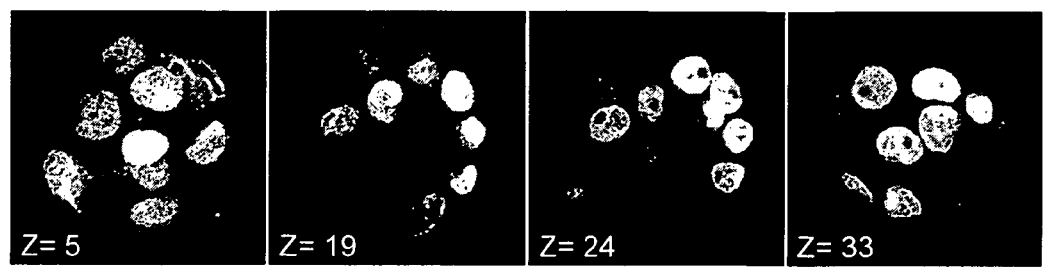
FIG. 19 shows confocal micrographs: optical z-axis sections (each section 1 µm thick) of a multicellular MCF 10A spheroid through the central lumen

MCF 10A spheroids are hollow with central lumen. Spheroids fixed and isolated from the hydrogels after being maintained in culture for a period of 13 days were hollow, with central lumina surrounded by a single layer of cells with basally-oriented nuclei, typical of mammary acini (FIG. 19). In some cases, acini contained one or two spindle-shaped, basally located cells reminiscent of myoepithelial cells, which stained positively for cytoplasmic laminin-5, and were in contact with cell-secreted basement membrane.

Figure 20:
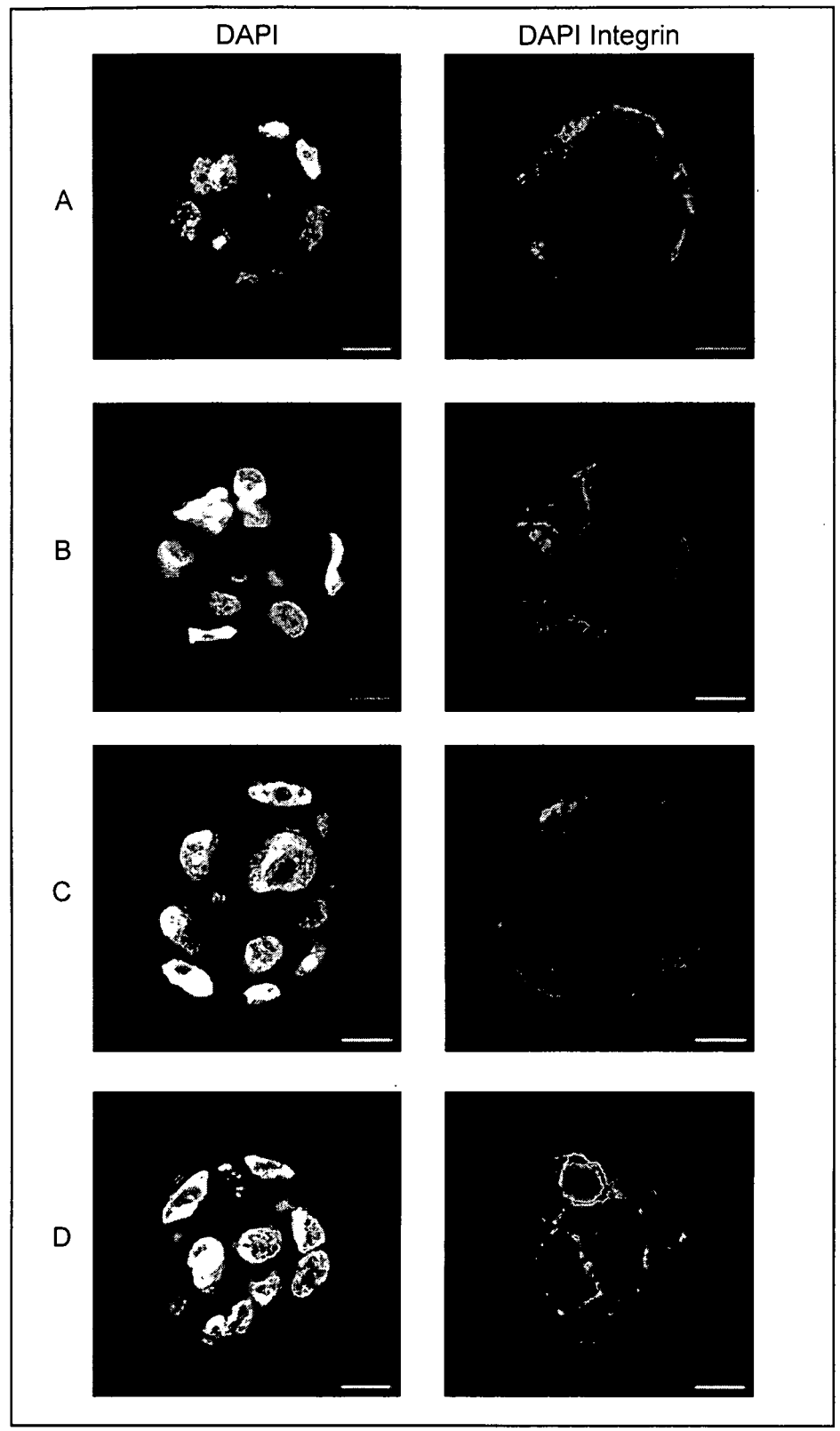
FIG. 20 shows basal localization of $\alpha3$ and $\beta4$ integrin (A and D, respectively), with lateral expression of $\beta1$ (B) and $\alpha6$ (C) integrin in MCF 10A acini on day 19 of 3D culture. DAPI nuclear stain. Scale bars measure 10 µm.
Figure 21:
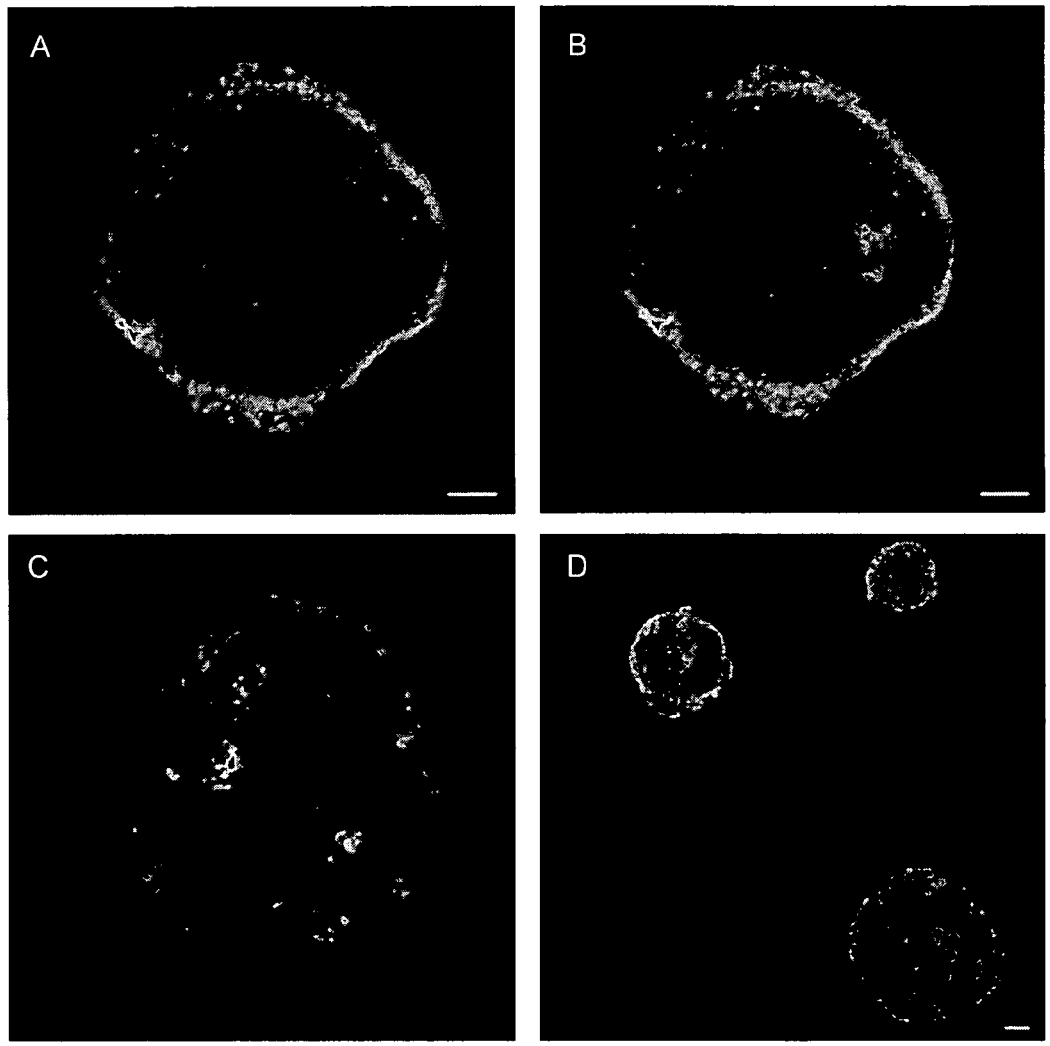
FIG. 21 shows MCF 10A acini in 3D culture demonstrating apicobasal polarity. A) basolateral expression of ZO-1, with B) corresponding nuclear DAPI (blue) activated caspase-3 (red), marking an apoptotic cell. Green in this image is ZO-1 C) apical localization of GM130 with basally staining β4 integrin, D) Basal staining of laminin (β1 subunit). In all the images, blue is DAPI nuclear stain, scale bars measure 10 µm.

MCF 10A acini exhibit apico-basal polarity in 3D culture. Acini formed by MCF 10A cultured in hydrogel matrices in the absence of exogenous laminin, demonstrated polarity, with golgi apparatus of acinar cells oriented towards the lumen (GM130 stain), and basal expression of integrin β4 (FIG. 21). We observed basolateral localization of integrin β4 and α3, and lateral expression of α6 and β1 integrin. (FIG. 20)

Figure 22:
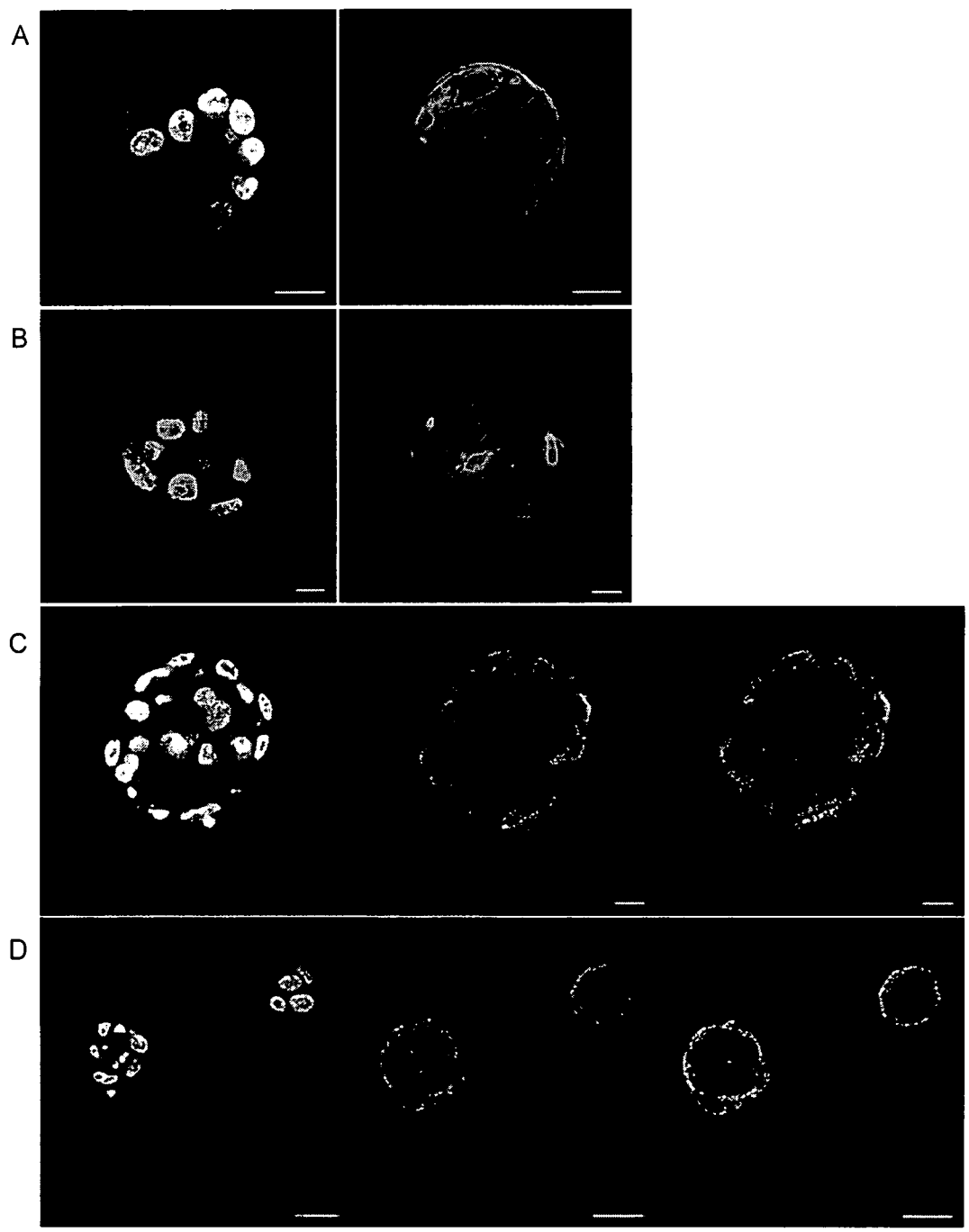
FIG. 22 shows secretion of basement membrane. A) Laminin V, B) laminin 1 and 2 stained simultaneously, C) is type IV collagen, D) is laminin B1 subunit. Blue is DAPI nuclear stain in all images, and scale bars measure 10 µm.

MCF 10A acini in 3D culture secrete endogenous basement membrane proteins. MCF 10A cells cultured in 3D synthetic integrin hydrogels secrete laminin and collagen IV, both of which are major components of native ECM. Day 13 acini showed basal expression of laminin 5 (FIG. 22A), with intraluminal proteinaceous material also staining positive for laminin 5 as well as other proteins, such as actin, possibly as debris from central apoptotic cells. Spindle-shaped cells on the periphery of the acini were also positive for laminin V. These cells also stained positive for cytokeratin-14, which is characteristic for myoepithelial cells. The acini in 3D culture were also positive for the β1 subunit of laminin, expressed basally (FIG. 22D), as well as laminin 1 and 2, of which there was no observable distinct pattern of localization (FIG. 22B). There was weak type IV collagen expression (FIG. 22C) which was localized basally at the periphery of the acini.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A cell adhesion matrix prepared by the process comprising:
    contacting a plurality of poly(vinyl alcohol) chains and at least one boronic acid crosslinker having at least two boronic acids in a mixture, under conditions such that each boronic acid becomes linked to two adjacent hydroxy groups of one of the plurality of poly(vinyl alcohol) chains, wherein
the boronic acid crosslinker is of formula I:

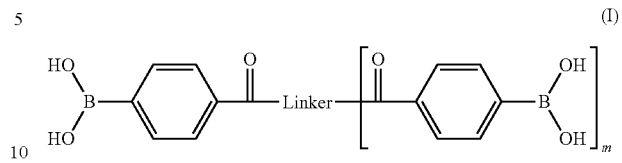

(I)

wherein
Linker comprises a biocompatible polymer selected from the group consisting of a poly(propylene glycol) polymer and a poly(ethylene glycol) polymer of the following formula:

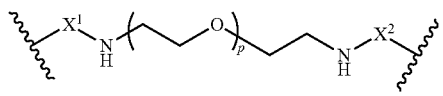

wherein
$X^1$ and $X^2$ are each independently selected from the group consisting of a bond, a branching moiety, lysine and a lysine derivative; and
subscript p is from about 10 to about 500;
subscript m is from about 1 to about 100; and
each poly(vinyl alcohol) shain is of formula II:

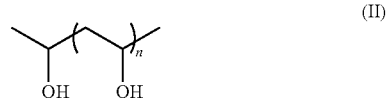

(II)

wherein subscript n is from about 10 to about 5000.

2. The cell adhesion matrix of claim 1, wherein the mixture further comprises a plurality of cells.

3. The cell adhesion matrix of claim 1, wherein the conditions include a pH of from about 7.0 to about 8.0.

4. The cell adhesion matrix of claim 1, wherein $X^1$ and $X^2$ are each a bond.

5. The cell adhesion matrix of claim 1, wherein $X^1$ and $X^2$ are each lysine.

6. The cell adhesion matrix of claim 1, wherein subscript p is from about 40 to about 50.

7. The cell adhesion matrix of claim 1, wherein the boronic acid crosslinker is selected from the group consisting of:

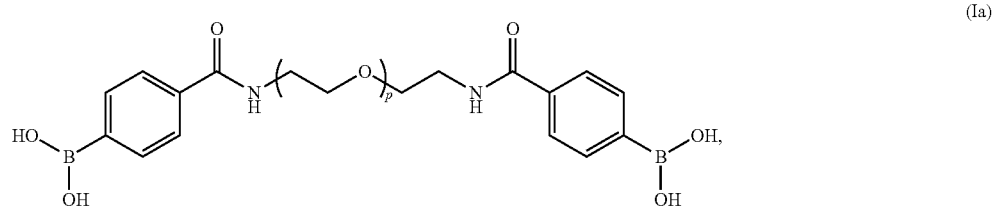

(Ia)

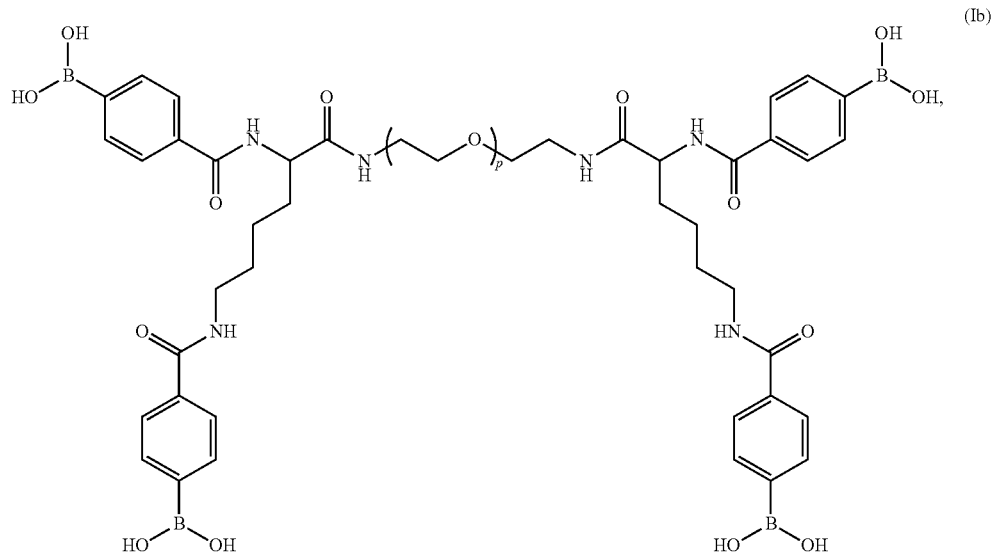
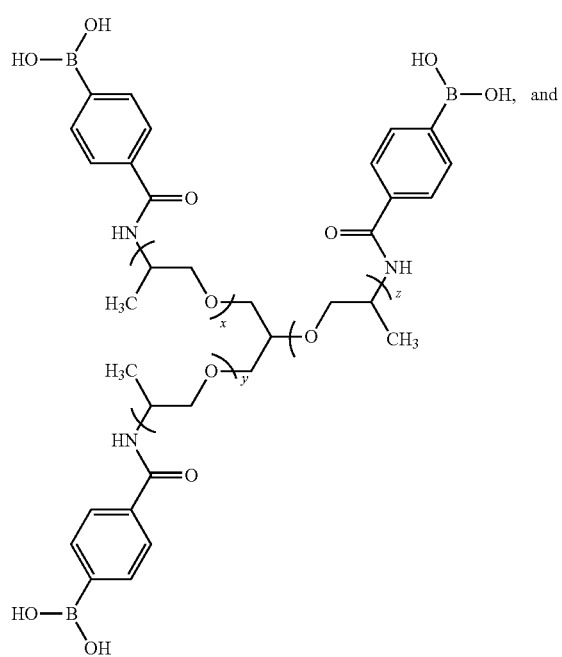

-continued

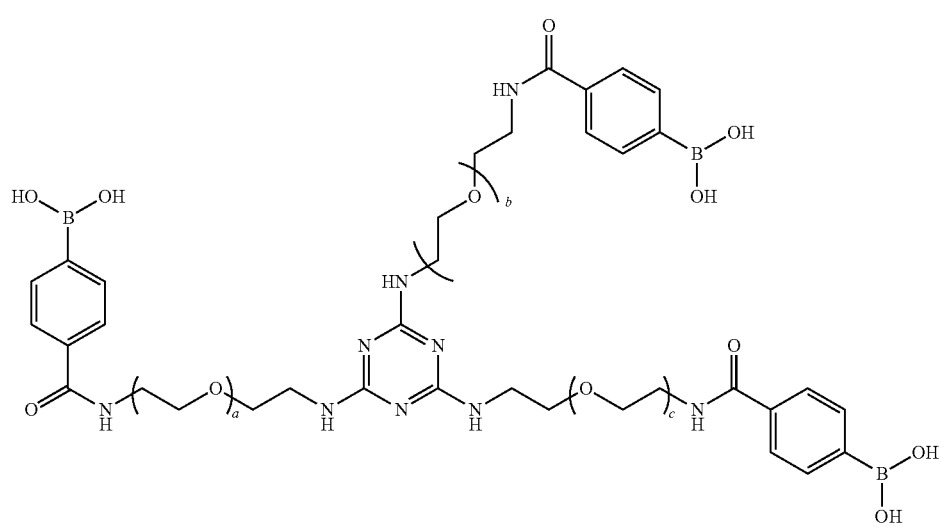

(Id)

wherein subscript p is from about 40 to about 50, subscripts x, y and z are each independently from 1 to about 75 such that x+y+z is from about 80 to about 90, and subscripts a, b and c are each independently from about 10 to about 100, such that a+b+c is from about 100 to about 200, at a pH of about 7.4 such that each boronic acid becomes linked to two adjacent hydroxy groups of one of the plurality of modified poly(vinyl alcohol) chains.

8. The cell adhesion matrix of claim 1, the process further comprising:
contacting a molecular recognition element conjugate and the plurality of poly(vinyl alcohol) chains in a mixture, wherein the molecular recognition element conjugate comprises a molecular recognition element and at least one binding group, under conditions such that each binding group of the molecular recognition element conjugate becomes linked to one of the poly(vinyl alcohol) chains.

9. The cell adhesion matrix of claim 8, wherein the molecular recognition element conjugate has the following formula III:

10. The cell adhesion matrix of claim 8, wherein the molecular recognition element is selected from the group consisting of LXY3, MSE, HYD1, LLP-2A, and RGD ligand.

11. The cell adhesion matrix of claim 1, wherein the poly (vinyl alcohol) is linked to at least one molecular recognition element.

12. A cell adhesion matrix comprising
at least one boronic acid crosslinker of formula I:

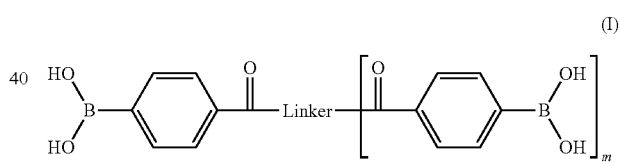

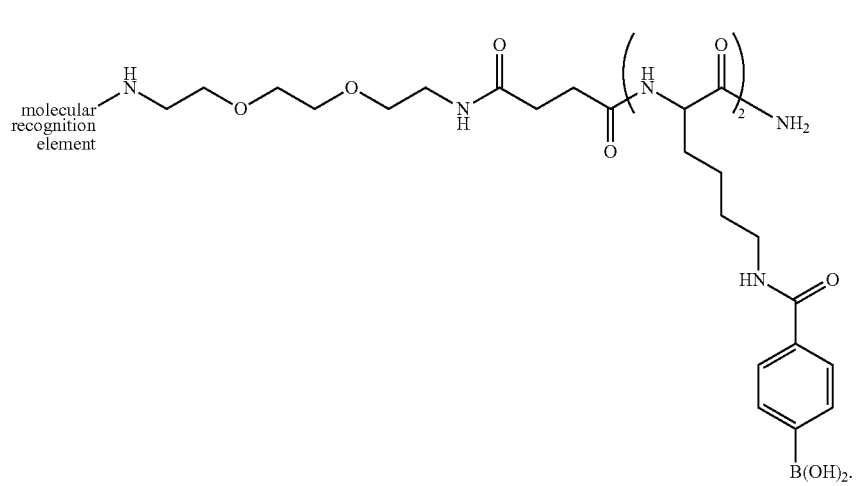

wherein

Linker comprises a biocompatible polymer selected from the group consisting of a poly(propylene glycol) polymer and a poly(ethylene glycol) polymer of the following formula:

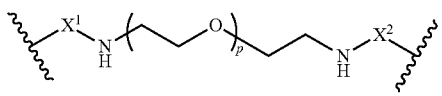

wherein

X$^1$ and X$^2$ are each independently selected from the group consisting of a bond, a branching moiety, lysine and a lysine derivative; and subscript p is from about 10 to about 500;

subscript m is from 1 to about 100; and a plurality of poly(vinyl alcohol) chains each of formula II:

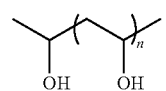

wherein subscript n is from about 10 to about 5000, wherein each boronic acid is linked to two adjacent hydroxy groups of one of the plurality of poly(vinyl alcohol) chains.

13. The cell adhesion matrix of claim 12, wherein the cell adhesion matrix further comprises a molecular recognition element conjugate.

14. The cell adhesion matrix of claim 12, wherein the cell adhesion matrix further comprises a cell.

15. A cell adhesion matrix prepared by the process comprising:

contacting a molecular recognition element conjugate of formula (III):

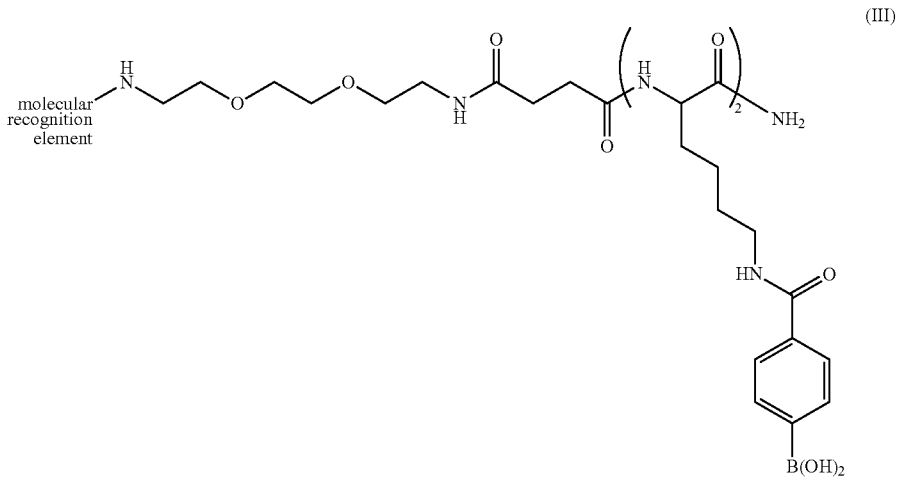

wherein the molecular recognition element is selected from the group consisting of LXY3, MSE, HYD1, LLP-2A, and RGD ligand, and a plurality of poly(vinyl alcohol) chains of formula (II):

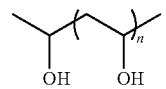

wherein subscript n is from about 10 to about 5000, at a pH of about 7.4 such that each boronic acid of the molecular recognition element conjugate becomes linked to two adjacent hydroxy groups of one of the poly(vinyl alcohol) chains to form a plurality of modified poly(vinyl alcohol) chains; and contacting the plurality of modified poly(vinyl alcohol) chains and at least one boronic acid crosslinker selected from the group consisting of:

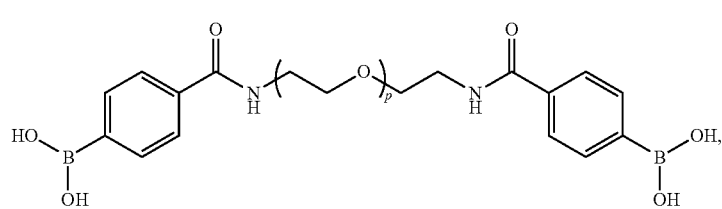
(Ia)
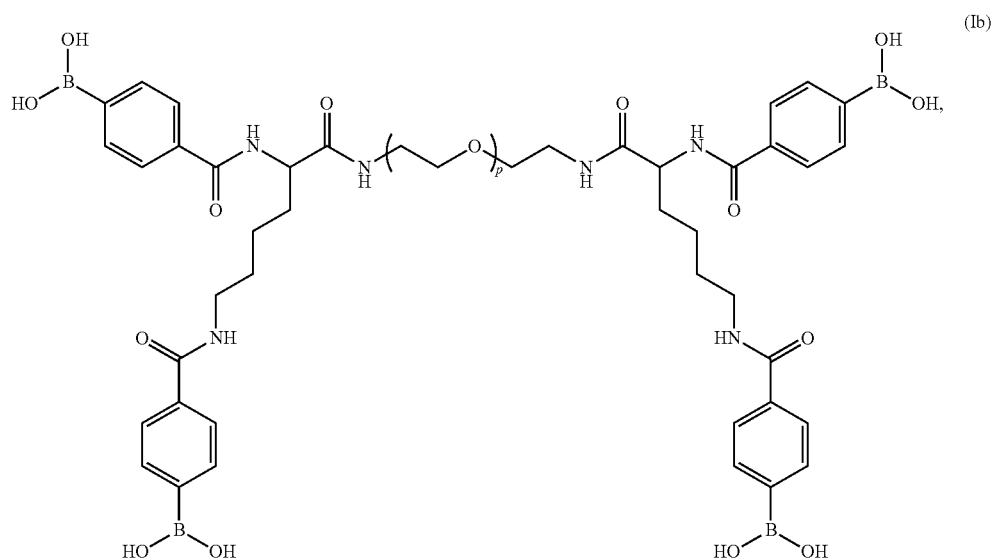
(Ib)
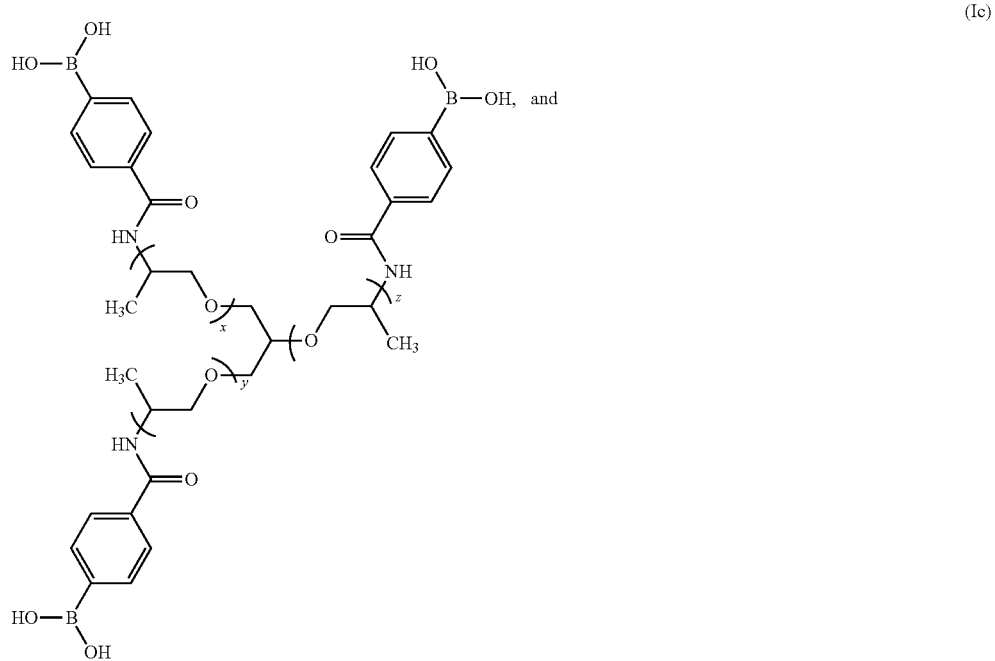
(Ic)

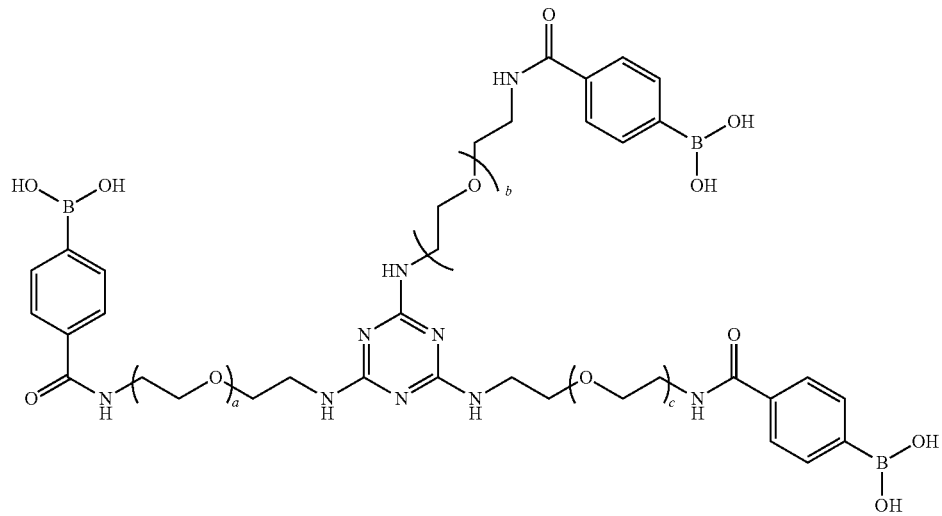

(Id)

wherein subscript p is from about 40 to about 50, subscripts x, y and z are each independently from 1 to about 75 such that x+y+z is from about 80 to about 90, and subscripts a, b and c are each independently from about 10 to about 100, such that a+b+c is from about 100 to about 200, at a pH of about 7.4 such that each boronic acid becomes linked to two adjacent hydroxy groups of one of the plurality of modified poly(vinyl alcohol) chains.

* * * * *